(12) United States Patent
Zacharias et al.

(10) Patent No.: US 8,066,755 B2
(45) Date of Patent: Nov. 29, 2011

(54) SYSTEM AND METHOD OF PIVOTED STENT DEPLOYMENT

(75) Inventors: Isaac J. Zacharias, Pleasanton, CA (US); Diego Aristizabal, Cloverdale, CA (US); Michael Mohn, Maple Grove, MN (US); Michael V. Chobotov, Santa Rosa, CA (US)

(73) Assignee: Trivascular, Inc., Santa Rosa, CA (US)

( * ) Notice: Subject to any disclaimer, the term of this patent is extended or adjusted under 35 U.S.C. 154(b) by 205 days.

(21) Appl. No.: 11/861,716

(22) Filed: Sep. 26, 2007

(65) Prior Publication Data
US 2009/0082844 A1    Mar. 26, 2009

(51) Int. Cl.
*A61F 2/06* (2006.01)
(52) U.S. Cl. .............. 623/1.12; 623/1.13; 623/1.14; 623/1.23; 623/1.36
(58) Field of Classification Search ........ 623/1.35–1.36, 623/1.11; 606/108
See application file for complete search history.

(56) References Cited

U.S. PATENT DOCUMENTS

| | | | |
|---|---|---|---|
| 3,076,737 A | 2/1963 | Roberts | |
| 3,540,431 A | 11/1970 | Uddin | |
| 3,631,854 A | 1/1972 | Fryer et al. | |
| 3,657,744 A | 4/1972 | Ersek | |
| 3,669,586 A | 6/1972 | Kramer | |
| 3,814,137 A | 6/1974 | Martinez | |
| 3,818,511 A | 6/1974 | Goldberg et al. | |
| 3,902,198 A | 9/1975 | Rathjen | |
| 3,991,767 A | 11/1976 | Miller et al. | |
| 4,096,227 A | 6/1978 | Gore | |
| 4,110,392 A | 8/1978 | Yamasaki | |
| 4,140,126 A | 2/1979 | Choudhury | |
| 4,183,102 A | 1/1980 | Guiset | |
| 4,187,390 A | 2/1980 | Gore | |
| 4,208,745 A | 6/1980 | Okita | |
| 4,214,587 A | 7/1980 | Sakura, Jr. | |
| 4,229,838 A | 10/1980 | Mano | |
| 4,248,924 A | 2/1981 | Okita | |
| 4,385,093 A | 5/1983 | Hubis | |
| 4,416,028 A | 11/1983 | Eriksson et al. | |
| 4,434,797 A | 3/1984 | Silander | |
| 4,459,252 A | 7/1984 | MacGregor | |

(Continued)

FOREIGN PATENT DOCUMENTS

EP    0646365    4/1995

(Continued)

OTHER PUBLICATIONS

Blum et al. "Abdominal aortic aneurysms: preliminary technical and clinical results with transfemoral placement of endovascular self-expanding stent-grafts" Radiology 198(1):25-31 (1996).

(Continued)

*Primary Examiner* — William H Matthews
*Assistant Examiner* — Jacqueline Woznicki
(74) *Attorney, Agent, or Firm* — Grant Anderson LLP

(57) ABSTRACT

The invention provides a stent-graft system comprising a graft member and a stent having a connection end interconnected with the graft member and a free end opposed thereto. A belt retaining structure is provided at the stent free end. A belt is releasably retained in the belt retaining structure and is configured to constrain the stent free end independent of the stent connection end. A method of securing at least one end of a stent-graft within a vessel is also provided.

6 Claims, 7 Drawing Sheets

U.S. PATENT DOCUMENTS

| | | | |
|---|---|---|---|
| 4,474,630 A | 10/1984 | Planck et al. | |
| 4,478,665 A | 10/1984 | Hubis | |
| 4,482,516 A | 11/1984 | Bowman et al. | |
| 4,497,074 A | 2/1985 | Rey et al. | |
| 4,503,569 A | 3/1985 | Dotter | |
| 4,512,338 A | 4/1985 | Balko et al. | |
| 4,550,447 A | 11/1985 | Seiler, Jr. et al. | |
| 4,552,707 A | 11/1985 | How | |
| 4,562,596 A | 1/1986 | Kornberg | |
| 4,577,631 A | 3/1986 | Kreamer | |
| 4,580,568 A | 4/1986 | Gianturco | |
| 4,592,754 A | 6/1986 | Gupte et al. | |
| 4,617,932 A | 10/1986 | Kornberg | |
| 4,647,416 A | 3/1987 | Seiler, Jr. et al. | |
| 4,655,769 A | 4/1987 | Zachariades | |
| 4,655,771 A | 4/1987 | Wallsten | |
| 4,665,906 A | 5/1987 | Jervis | |
| 4,705,517 A | 11/1987 | DiPisa, Jr. | |
| 4,731,073 A | 3/1988 | Robinson | |
| 4,733,665 A | 3/1988 | Palmaz | |
| 4,739,762 A | 4/1988 | Palmaz | |
| 4,740,207 A | 4/1988 | Kreamer | |
| 4,743,480 A | 5/1988 | Campbell et al. | |
| 4,760,102 A | 7/1988 | Moriyama et al. | |
| 4,776,337 A | 10/1988 | Palmaz | |
| 4,787,899 A | 11/1988 | Lazarus | |
| 4,816,028 A | 3/1989 | Kapadia et al. | |
| 4,830,003 A | 5/1989 | Wolff et al. | |
| 4,856,516 A | 8/1989 | Hillstead | |
| 4,871,365 A | 10/1989 | Dumican | |
| 4,877,661 A | 10/1989 | House et al. | |
| 4,902,423 A | 2/1990 | Bacino | |
| 4,932,938 A | 6/1990 | Goldberg et al. | |
| 4,941,870 A | 7/1990 | Okada et al. | |
| 4,955,899 A | 9/1990 | Della et al. | |
| 4,957,669 A | 9/1990 | Primm | |
| 4,985,296 A | 1/1991 | Mortimer, Jr. | |
| 4,994,071 A | 2/1991 | MacGregor | |
| 4,994,077 A | 2/1991 | Dobben | |
| 5,019,090 A | 5/1991 | Pinchuk | |
| 5,041,126 A | 8/1991 | Gianturco | |
| 5,052,998 A | 10/1991 | Zimmon | |
| 5,059,211 A | 10/1991 | Stack et al. | |
| 5,064,435 A | 11/1991 | Porter | |
| 5,098,625 A | 3/1992 | Huang et al. | |
| 5,100,422 A | 3/1992 | Berguer et al. | |
| 5,104,399 A | 4/1992 | Lazarus | |
| 5,104,400 A | 4/1992 | Berguer et al. | |
| 5,104,404 A | 4/1992 | Wolff | |
| 5,108,424 A | 4/1992 | Hoffman, Jr. et al. | |
| 5,110,527 A | 5/1992 | Harada et al. | |
| 5,116,365 A | 5/1992 | Hillstead | |
| 5,122,154 A | 6/1992 | Rhodes | |
| 5,123,917 A | 6/1992 | Lee | |
| 5,133,732 A | 7/1992 | Wiktor | |
| 5,135,536 A | 8/1992 | Hillstead | |
| 5,139,480 A | 8/1992 | Hickle et al. | |
| 5,150,304 A | 9/1992 | Berchem et al. | |
| 5,151,105 A | 9/1992 | Kwan-Gett | |
| 5,152,782 A | 10/1992 | Kowligi et al. | |
| 5,156,620 A | 10/1992 | Pigott | |
| 5,163,955 A | 11/1992 | Love | |
| 5,167,614 A | 12/1992 | Tessmann | |
| 5,171,262 A | 12/1992 | MacGregor | |
| 5,192,310 A | 3/1993 | Herweck et al. | |
| 5,195,984 A | 3/1993 | Schatz | |
| 5,197,976 A | 3/1993 | Herweck et al. | |
| 5,197,978 A | 3/1993 | Hess | |
| 5,201,757 A | 4/1993 | Heyn et al. | |
| 5,202,352 A | 4/1993 | Okada et al. | |
| 5,207,695 A | 5/1993 | Trout, III | |
| 5,217,483 A | 6/1993 | Tower | |
| 5,219,355 A | 6/1993 | Parodi et al. | |
| 5,226,913 A | 7/1993 | Pinchuk | |
| 5,234,456 A | 8/1993 | Silvestini | |
| 5,250,059 A | 10/1993 | Andreas et al. | |
| 5,275,622 A | 1/1994 | Lazarus et al. | |
| 5,282,823 A | 2/1994 | Schwartz et al. | |
| 5,282,824 A | 2/1994 | Gianturco | |
| 5,282,847 A | 2/1994 | Trescony et al. | |
| 5,290,305 A | 3/1994 | Inoue | |
| 5,292,331 A | 3/1994 | Boneau | |
| 5,304,200 A | 4/1994 | Spaulding | |
| 5,314,472 A | 5/1994 | Fontaine | |
| 5,316,023 A | 5/1994 | Palmaz et al. | |
| 5,320,100 A | 6/1994 | Herweck et al. | |
| 5,321,109 A | 6/1994 | Bosse et al. | |
| 5,330,528 A | 7/1994 | Lazim | |
| 5,334,164 A | 8/1994 | Guy et al. | |
| 5,334,201 A | 8/1994 | Cowan | |
| 5,344,426 A | 9/1994 | Lau et al. | |
| 5,344,444 A | 9/1994 | Glastra | |
| 5,344,451 A | 9/1994 | Dayton | |
| 5,350,398 A | 9/1994 | Pavcnik | |
| 5,354,310 A | 10/1994 | Garnic et al. | |
| 5,354,329 A | 10/1994 | Whalen | |
| 5,360,443 A | 11/1994 | Barone et al. | |
| 5,365,996 A | 11/1994 | Crook | |
| 5,366,504 A | 11/1994 | Andersen et al. | |
| 5,370,682 A | 12/1994 | Schmitt | |
| 5,370,691 A | 12/1994 | Samson | |
| 5,374,473 A | 12/1994 | Knox et al. | |
| 5,382,261 A | 1/1995 | Palmaz | |
| 5,383,892 A | 1/1995 | Cardon et al. | |
| 5,383,928 A | 1/1995 | Scott et al. | |
| 5,387,235 A | 2/1995 | Chuter et al. | |
| 5,389,106 A | 2/1995 | Tower et al. | |
| 5,391,147 A | 2/1995 | Imran et al. | |
| 5,397,345 A | 3/1995 | Lazarus | |
| 5,405,377 A | 4/1995 | Cragg | |
| 5,405,378 A | 4/1995 | Strecker | |
| 5,405,379 A | 4/1995 | Lane | |
| 5,411,550 A | 5/1995 | Herweck et al. | |
| 5,415,634 A | 5/1995 | Glynn et al. | |
| 5,423,851 A | 6/1995 | Samuels | |
| 5,433,909 A | 7/1995 | Martakos et al. | |
| 5,437,900 A | 8/1995 | Kuzowski | |
| 5,441,515 A | 8/1995 | Khosravi et al. | |
| 5,443,458 A | 8/1995 | Eury | |
| 5,443,498 A | 8/1995 | Fountaine | |
| 5,445,646 A | 8/1995 | Euteneuer et al. | |
| 5,447,152 A | 9/1995 | Kohsai et al. | |
| 5,449,373 A | 9/1995 | Pinchasik et al. | |
| 5,456,713 A | 10/1995 | Chuter | |
| 5,464,419 A | 11/1995 | Glastra | |
| 5,464,449 A | 11/1995 | Ryan et al. | |
| 5,466,509 A | 11/1995 | Kowllgl et al. | |
| 5,474,824 A | 12/1995 | Martakos et al. | |
| 5,476,506 A | 12/1995 | Lunn | |
| 5,476,589 A | 12/1995 | Bacino | |
| 5,478,330 A | 12/1995 | Imran et al. | |
| 5,480,423 A | 1/1996 | Ravenscroft et al. | |
| 5,489,295 A | 2/1996 | Piplani et al. | |
| 5,505,887 A | 4/1996 | Zdrahala et al. | |
| 5,507,769 A | 4/1996 | Marin et al. | |
| 5,507,770 A | 4/1996 | Turk | |
| 5,512,360 A | 4/1996 | King | |
| 5,514,154 A | 5/1996 | Lau et al. | |
| 5,522,880 A | 6/1996 | Barone et al. | |
| 5,522,881 A | 6/1996 | Lentz | |
| 5,522,883 A | 6/1996 | Slater et al. | |
| 5,524,633 A | 6/1996 | Heaven et al. | |
| 5,527,353 A | 6/1996 | Schmitt | |
| 5,527,355 A | 6/1996 | Ahn | |
| 5,529,653 A | 6/1996 | Glastra | |
| 5,529,820 A | 6/1996 | Nomi et al. | |
| 5,534,024 A | 7/1996 | Rogers et al. | |
| 5,536,274 A | 7/1996 | Neuss | |
| 5,545,135 A | 8/1996 | Iacob et al. | |
| 5,549,662 A | 8/1996 | Fordenbacher | |
| 5,549,663 A | 8/1996 | Cottone, Jr. | |
| 5,552,100 A | 9/1996 | Shannon et al. | |
| 5,554,180 A | 9/1996 | Turk | |
| 5,554,181 A | 9/1996 | Das | |
| 5,554,183 A | 9/1996 | Nazari | |
| 5,554,185 A | 9/1996 | Block et al. | |
| 5,556,414 A | 9/1996 | Turi | |

| | | |
|---|---|---|
| 5,556,426 A | 9/1996 | Popadiuk et al. |
| 5,560,986 A | 10/1996 | Mortimer, Jr. |
| 5,562,697 A | 10/1996 | Christiansen |
| 5,562,724 A | 10/1996 | Vorwerk et al. |
| 5,562,726 A | 10/1996 | Chuter |
| 5,562,727 A | 10/1996 | Turk et al. |
| 5,562,728 A | 10/1996 | Lazarus et al. |
| 5,569,295 A | 10/1996 | Lam |
| 5,571,171 A | 11/1996 | Barone et al. |
| 5,571,172 A | 11/1996 | Chin |
| 5,571,173 A | 11/1996 | Parodi |
| 5,575,817 A | 11/1996 | Martin |
| 5,575,818 A | 11/1996 | Pinchuk |
| 5,578,071 A | 11/1996 | Parodi |
| 5,578,072 A | 11/1996 | Barone et al. |
| 5,588,964 A | 12/1996 | Imran et al. |
| 5,591,195 A | 1/1997 | Taheri et al. |
| 5,591,197 A | 1/1997 | Orth et al. |
| 5,591,229 A | 1/1997 | Parodi |
| 5,597,378 A | 1/1997 | Jervis |
| 5,603,721 A | 2/1997 | Lau et al. |
| 5,607,478 A | 3/1997 | Lentz et al. |
| 5,609,624 A | 3/1997 | Kalis |
| 5,609,625 A | 3/1997 | Piplani et al. |
| 5,609,627 A | 3/1997 | Goicoechea et al. |
| 5,609,628 A | 3/1997 | Keranen |
| 5,609,629 A | 3/1997 | Fearnont |
| 5,612,885 A | 3/1997 | Love |
| 5,618,301 A | 4/1997 | Hauenstein et al. |
| 5,620,763 A | 4/1997 | House et al. |
| 5,626,599 A | 5/1997 | Bourne et al. |
| 5,628,783 A | 5/1997 | Quiachon et al. |
| 5,628,786 A | 5/1997 | Banas et al. |
| 5,628,788 A | 5/1997 | Pinchuk |
| 5,630,829 A | 5/1997 | Lauterjung |
| 5,632,772 A | 5/1997 | Alcime et al. |
| 5,632,840 A | 5/1997 | Campbell |
| 5,639,278 A | 6/1997 | Dereume et al. |
| 5,641,373 A | 6/1997 | Shannon et al. |
| 5,645,915 A | 7/1997 | Kranzler et al. |
| 5,649,978 A | 7/1997 | Samson |
| 5,653,745 A | 8/1997 | Trescony et al. |
| 5,653,746 A | 8/1997 | Schmitt |
| 5,656,029 A | 8/1997 | Imran et al. |
| 5,662,675 A | 9/1997 | Stockert et al. |
| 5,662,700 A | 9/1997 | Lazarus |
| 5,665,115 A | 9/1997 | Cragg |
| 5,665,117 A | 9/1997 | Rhodes |
| 5,667,523 A | 9/1997 | Bynon et al. |
| 5,669,936 A | 9/1997 | Lazarus |
| 5,676,671 A | 10/1997 | Inoue |
| 5,676,696 A | 10/1997 | Marcade |
| 5,676,697 A | 10/1997 | McDonald |
| 5,681,346 A | 10/1997 | Orth et al. |
| 5,683,449 A | 11/1997 | Marcade |
| 5,683,451 A | 11/1997 | Lenker et al. |
| 5,683,453 A | 11/1997 | Palmaz |
| 5,690,644 A | 11/1997 | Yurek et al. |
| 5,693,083 A | 12/1997 | Baker et al. |
| 5,693,084 A | 12/1997 | Chuter |
| 5,693,087 A | 12/1997 | Parodi |
| 5,693,088 A | 12/1997 | Lazarus |
| 5,697,968 A | 12/1997 | Rogers et al. |
| 5,697,971 A | 12/1997 | Fischell et al. |
| 5,700,285 A | 12/1997 | Myers et al. |
| 5,707,378 A | 1/1998 | Ahn et al. |
| 5,707,388 A | 1/1998 | Lauterjung |
| 5,708,044 A | 1/1998 | Branca |
| 5,709,701 A | 1/1998 | Parodi |
| 5,709,703 A | 1/1998 | Lukie et al. |
| 5,712,315 A | 1/1998 | Dolan |
| 5,713,917 A | 2/1998 | Leonhardt et al. |
| 5,716,393 A | 2/1998 | Lindenberg et al. |
| 5,716,395 A | 2/1998 | Myers et al. |
| 5,718,159 A | 2/1998 | Thompson |
| 5,718,973 A | 2/1998 | Lewis et al. |
| 5,720,776 A | 2/1998 | Chuter et al. |
| 5,723,004 A | 3/1998 | Dereume et al. |
| 5,725,547 A | 3/1998 | Chuter |
| 5,725,549 A | 3/1998 | Lam |
| 5,728,131 A | 3/1998 | Frantzen et al. |
| 5,733,303 A | 3/1998 | Israel et al. |
| 5,733,325 A | 3/1998 | Robinson et al. |
| 5,735,892 A | 4/1998 | Myers et al. |
| 5,735,893 A | 4/1998 | Lau et al. |
| 5,735,897 A | 4/1998 | Buirge |
| 5,741,324 A | 4/1998 | Glastra |
| 5,741,325 A | 4/1998 | Chaikof et al. |
| 5,747,128 A | 5/1998 | Campbell et al. |
| 5,749,880 A | 5/1998 | Banas et al. |
| 5,749,894 A | 5/1998 | Engleson |
| 5,749,920 A | 5/1998 | Quiachon et al. |
| 5,749,921 A | 5/1998 | Lenker et al. |
| 5,755,772 A | 5/1998 | Evans et al. |
| 5,755,776 A | 5/1998 | Al-Saadon |
| 5,766,203 A | 6/1998 | Imran et al. |
| 5,769,882 A | 6/1998 | Fogarty et al. |
| 5,769,885 A | 6/1998 | Quiachon et al. |
| 5,769,887 A | 6/1998 | Brown et al. |
| 5,772,884 A | 6/1998 | Tanaka et al. |
| 5,776,142 A | 7/1998 | Gunderson |
| 5,776,161 A | 7/1998 | Globerman |
| 5,776,183 A | 7/1998 | Kanesaka et al. |
| 5,780,807 A | 7/1998 | Saunders |
| 5,782,789 A | 7/1998 | Herweck et al. |
| 5,782,838 A | 7/1998 | Beyar et al. |
| 5,782,904 A | 7/1998 | White et al. |
| 5,782,909 A | 7/1998 | Quiachon et al. |
| 5,785,679 A | 7/1998 | Abolfathi et al. |
| 5,788,626 A | 8/1998 | Thompson |
| 5,789,047 A | 8/1998 | Sasaki et al. |
| 5,797,951 A | 8/1998 | Mueller |
| 5,798,924 A | 8/1998 | Eufinger et al. |
| 5,799,384 A | 9/1998 | Schwartz et al. |
| 5,800,508 A | 9/1998 | Goicoechea et al. |
| 5,800,512 A | 9/1998 | Lentz et al. |
| 5,800,515 A | 9/1998 | Nadal et al. |
| 5,800,518 A | 9/1998 | Piplani et al. |
| 5,800,522 A | 9/1998 | Campbell et al. |
| 5,800,524 A | 9/1998 | Borghi |
| 5,800,526 A | 9/1998 | Anderson et al. |
| 5,810,870 A | 9/1998 | Myers et al. |
| 5,810,872 A | 9/1998 | Kanesaka et al. |
| 5,814,405 A | 9/1998 | Branca et al. |
| 5,817,102 A | 10/1998 | Liann et al. |
| 5,824,037 A | 10/1998 | Fogarty et al. |
| 5,824,039 A | 10/1998 | Piplani et al. |
| 5,824,041 A | 10/1998 | Lenker et al. |
| 5,824,042 A | 10/1998 | Lombardi et al. |
| 5,824,044 A | 10/1998 | Quiachon et al. |
| 5,824,046 A | 10/1998 | Smith et al. |
| 5,824,058 A | 10/1998 | Ravenscroft et al. |
| 5,827,289 A | 10/1998 | Reiley et al. |
| 5,827,310 A | 10/1998 | Spoeistra |
| 5,827,320 A | 10/1998 | Richter et al. |
| 5,827,321 A | 10/1998 | Roubin et al. |
| 5,833,651 A | 11/1998 | Donovan et al. |
| 5,833,707 A | 11/1998 | Mcintyre et al. |
| 5,836,964 A | 11/1998 | Richter et al. |
| 5,836,966 A | 11/1998 | St. Germain |
| 5,840,775 A | 11/1998 | Howard, Jr. et al. |
| 5,843,158 A * | 12/1998 | Lenker et al. ................ 623/1.13 |
| 5,843,160 A | 12/1998 | Rhodes |
| 5,843,162 A | 12/1998 | Inoue |
| 5,843,164 A | 12/1998 | Frantzen et al. |
| 5,843,166 A | 12/1998 | Lentz et al. |
| 5,843,167 A | 12/1998 | Dwyer et al. |
| 5,843,170 A | 12/1998 | Ahn |
| 5,843,173 A | 12/1998 | Shannon et al. |
| 5,843,175 A | 12/1998 | Frantzen |
| 5,853,419 A | 12/1998 | Imran |
| 5,855,598 A | 1/1999 | Pinchuk |
| 5,858,556 A | 1/1999 | Eckert et al. |
| 5,861,027 A | 1/1999 | Trapp |
| 5,871,536 A | 2/1999 | Lazarus |
| 5,871,537 A | 2/1999 | Holman et al. |
| 5,871,538 A | 2/1999 | Dereume |
| 5,873,906 A | 2/1999 | Lau et al. |

| Patent | Date | Inventor |
|---|---|---|
| 5,876,432 A | 3/1999 | Lau et al. |
| 5,891,193 A | 4/1999 | Robinson et al. |
| 5,904,713 A | 5/1999 | Leschinsky |
| 5,906,619 A | 5/1999 | Olson et al. |
| 5,906,641 A | 5/1999 | Thompson et al. |
| 5,910,168 A | 6/1999 | Myers et al. |
| 5,910,277 A | 6/1999 | Ishlno et al. |
| 5,911,754 A | 6/1999 | Kanesaka et al. |
| 5,916,264 A | 6/1999 | Von Oepen et al. |
| 5,919,204 A | 7/1999 | Lukic et al. |
| 5,922,020 A | 7/1999 | Klein et al. |
| 5,925,061 A | 7/1999 | Ogi et al. |
| 5,925,075 A | 7/1999 | Myers et al. |
| 5,931,865 A | 8/1999 | Silverman et al. |
| 5,935,667 A | 8/1999 | Calcote et al. |
| 5,939,198 A | 8/1999 | Howard, Jr. et al. |
| 5,944,750 A | 8/1999 | Tanner et al. |
| 5,948,016 A | 9/1999 | Jang |
| 5,954,729 A | 9/1999 | Bachmann et al. |
| 5,955,016 A | 9/1999 | Goldfarb |
| 5,957,973 A | 9/1999 | Quiachon et al. |
| 5,961,545 A | 10/1999 | Lentz et al. |
| 5,961,546 A | 10/1999 | Robinson et al. |
| 5,968,068 A | 10/1999 | Dehdashtian et al. |
| 5,968,090 A | 10/1999 | Ratcliff et al. |
| 5,972,023 A | 10/1999 | Tanner et al. |
| 5,972,027 A | 10/1999 | Johnson |
| 5,972,441 A | 10/1999 | Campbell et al. |
| 5,976,155 A | 11/1999 | Foreman et al. |
| 5,976,179 A | 11/1999 | Inoue |
| 5,976,192 A | 11/1999 | McIntyre et al. |
| 5,976,650 A | 11/1999 | Campbell et al. |
| 5,980,530 A | 11/1999 | Willard et al. |
| 5,980,570 A | 11/1999 | Simpson |
| 5,984,955 A | 11/1999 | Wisselink |
| 5,984,956 A | 11/1999 | Tweden et al. |
| 5,984,964 A | 11/1999 | Roberts et al. |
| 5,989,287 A | 11/1999 | Yang et al. |
| 5,993,481 A | 11/1999 | Marcade et al. |
| 5,993,489 A | 11/1999 | Lewis et al. |
| 5,997,573 A | 12/1999 | Quijano et al. |
| 6,001,123 A | 12/1999 | Lau |
| 6,004,346 A | 12/1999 | Wolff et al. |
| 6,004,347 A | 12/1999 | McNamara et al. |
| 6,004,348 A | 12/1999 | Banas et al. |
| 6,007,575 A | 12/1999 | Samuels |
| 6,015,429 A | 1/2000 | Lau et al. |
| 6,015,431 A | 1/2000 | Thornton et al. |
| 6,015,432 A | 1/2000 | Rakos et al. |
| 6,017,362 A | 1/2000 | Lau |
| 6,017,364 A | 1/2000 | Lazarus |
| 6,019,778 A | 2/2000 | Wilson et al. |
| 6,019,779 A | 2/2000 | Thorud et al. |
| 6,019,787 A | 2/2000 | Richard et al. |
| 6,022,359 A | 2/2000 | Frantzen |
| 6,024,763 A | 2/2000 | Lenker et al. |
| 6,025,044 A | 2/2000 | Campbell et al. |
| 6,027,779 A | 2/2000 | Campbell et al. |
| 6,027,811 A | 2/2000 | Campbell et al. |
| 6,030,413 A | 2/2000 | Lazarus |
| 6,030,414 A | 2/2000 | Taheri |
| 6,030,415 A | 2/2000 | Chuter |
| 6,036,640 A | 3/2000 | Corace et al. |
| 6,036,702 A | 3/2000 | Bachinski et al. |
| 6,036,723 A | 3/2000 | Anidjar et al. |
| 6,036,724 A | 3/2000 | Lentz et al. |
| 6,036,725 A | 3/2000 | Avellanet |
| 6,039,754 A | 3/2000 | Caro |
| 6,039,758 A | 3/2000 | Quiachon et al. |
| 6,042,589 A | 3/2000 | Marianne |
| 6,042,605 A | 3/2000 | Martin et al. |
| 6,042,606 A | 3/2000 | Frantzen |
| 6,045,557 A | 4/2000 | White et al. |
| 6,048,484 A | 4/2000 | House et al. |
| 6,051,020 A | 4/2000 | Goicoechea et al. |
| 6,053,943 A | 4/2000 | Edwin et al. |
| 6,059,821 A | 5/2000 | Anidjar et al. |
| 6,059,823 A | 5/2000 | Holman et al. |
| 6,060,534 A | 5/2000 | Ronan et al. |
| 6,063,114 A | 5/2000 | Nash et al. |
| 6,068,626 A | 5/2000 | Harrington et al. |
| 6,070,589 A | 6/2000 | Keith et al. |
| 6,074,341 A | 6/2000 | Anderson et al. |
| 6,075,180 A | 6/2000 | Sharber et al. |
| 6,077,296 A | 6/2000 | Shokoohi et al. |
| 6,077,297 A | 6/2000 | Robinson et al. |
| 6,077,298 A | 6/2000 | Tu et al. |
| 6,090,128 A | 7/2000 | Douglas |
| 6,093,203 A | 7/2000 | Uflacker |
| 6,096,052 A | 8/2000 | Callister et al. |
| 6,096,070 A | 8/2000 | Ragheb et al. |
| 6,098,630 A | 8/2000 | Papazoglou |
| 6,102,918 A | 8/2000 | Kerr |
| 6,102,938 A | 8/2000 | Evans et al. |
| 6,102,940 A | 8/2000 | Robichon et al. |
| 6,103,172 A | 8/2000 | Newman et al. |
| 6,106,548 A | 8/2000 | Roubin et al. |
| 6,110,198 A | 8/2000 | Fogarty et al. |
| 6,113,628 A | 9/2000 | Borghi |
| 6,117,168 A | 9/2000 | Yang et al. |
| 6,123,722 A | 9/2000 | Fogarty et al. |
| 6,124,523 A | 9/2000 | Banas et al. |
| 6,126,685 A | 10/2000 | Lenker et al. |
| 6,129,756 A | 10/2000 | Kugler et al. |
| 6,132,457 A | 10/2000 | Chobotov |
| 6,132,459 A | 10/2000 | Piplani et al. |
| 6,139,572 A | 10/2000 | Campbell et al. |
| 6,142,973 A | 11/2000 | Carleton et al. |
| 6,143,014 A | 11/2000 | Dehdashtian et al. |
| 6,143,015 A | 11/2000 | Nobles |
| 6,143,016 A | 11/2000 | Bleam et al. |
| 6,143,021 A | 11/2000 | Staehle |
| 6,143,022 A | 11/2000 | Shull et al. |
| 6,146,389 A | 11/2000 | Geitz |
| 6,146,416 A | 11/2000 | Andersen et al. |
| 6,146,417 A | 11/2000 | Ischinger |
| 6,149,665 A | 11/2000 | Gabbay |
| 6,149,681 A | 11/2000 | Houser et al. |
| 6,149,682 A | 11/2000 | Frid |
| 6,152,944 A | 11/2000 | Holman et al. |
| 6,152,956 A | 11/2000 | Pierce |
| 6,156,063 A | 12/2000 | Douglas |
| 6,156,064 A | 12/2000 | Chouinard |
| 6,159,229 A | 12/2000 | Jendersee et al. |
| 6,159,237 A | 12/2000 | Alt et al. |
| 6,159,238 A | 12/2000 | Killion et al. |
| 6,159,239 A | 12/2000 | Greenhalgh |
| 6,159,565 A | 12/2000 | Campbell et al. |
| 6,162,243 A | 12/2000 | Gray et al. |
| 6,162,245 A | 12/2000 | Jayaraman |
| 6,162,246 A | 12/2000 | Barone |
| 6,165,210 A | 12/2000 | Lau et al. |
| 6,165,211 A | 12/2000 | Thompson |
| 6,165,212 A | 12/2000 | Dereume et al. |
| 6,165,213 A | 12/2000 | Goicoechea et al. |
| 6,165,214 A | 12/2000 | Lazarus |
| 6,168,610 B1 | 1/2001 | Marin et al. |
| 6,168,614 B1 | 1/2001 | Andersen et al. |
| 6,168,616 B1 | 1/2001 | Brown, III |
| 6,168,617 B1 | 1/2001 | Blaeser et al. |
| 6,168,618 B1 | 1/2001 | Frantzen |
| 6,168,619 B1 | 1/2001 | Dinh et al. |
| 6,168,620 B1 | 1/2001 | Kerr |
| 6,174,326 B1 | 1/2001 | Kitaoka et al. |
| 6,183,481 B1 | 2/2001 | Lee et al. |
| 6,183,504 B1 | 2/2001 | Inoue |
| 6,187,034 B1 | 2/2001 | Frantzen |
| 6,187,036 B1 | 2/2001 | Shaolian et al. |
| 6,187,054 B1 | 2/2001 | Colone et al. |
| 6,193,745 B1 | 2/2001 | Fogarty et al. |
| 6,196,230 B1 | 3/2001 | Hall et al. |
| 6,197,046 B1 | 3/2001 | Piplani et al. |
| 6,197,049 B1 | 3/2001 | Shaolian et al. |
| 6,200,339 B1 | 3/2001 | Leschinsky et al. |
| 6,203,550 B1 | 3/2001 | Olson |
| 6,203,568 B1 | 3/2001 | Lombardi et al. |
| 6,203,569 B1 | 3/2001 | Wijay |
| 6,203,735 B1 | 3/2001 | Edwin et al. |

| | | |
|---|---|---|
| 6,203,779 B1 | 3/2001 | Ricci et al. |
| 6,210,422 B1 | 4/2001 | Douglas |
| 6,210,434 B1 | 4/2001 | Quiachon et al. |
| 6,210,435 B1 | 4/2001 | Piplani et al. |
| 6,214,038 B1 | 4/2001 | Piplani et al. |
| 6,214,039 B1 | 4/2001 | Banas et al. |
| 6,217,608 B1 | 4/2001 | Penn et al. |
| 6,221,102 B1 | 4/2001 | Baker et al. |
| 6,224,609 B1 | 5/2001 | Ressemann et al. |
| 6,231,562 B1 | 5/2001 | Khosravi et al. |
| 6,235,050 B1 | 5/2001 | Quiachon et al. |
| 6,235,051 B1 | 5/2001 | Murphy |
| 6,238,432 B1 | 5/2001 | Parodi |
| 6,240,616 B1 | 6/2001 | Yan |
| 6,241,759 B1 | 6/2001 | Piplani et al. |
| 6,245,097 B1 | 6/2001 | Inoue |
| 6,245,099 B1 | 6/2001 | Edwin et al. |
| 6,245,100 B1 | 6/2001 | Davila et al. |
| 6,245,101 B1 | 6/2001 | Drasler et al. |
| 6,245,102 B1 | 6/2001 | Jayaraman |
| 6,248,116 B1 | 6/2001 | Chevillon et al. |
| 6,251,132 B1 | 6/2001 | Ravenscroft et al. |
| 6,251,136 B1 | 6/2001 | Guruwaiya et al. |
| 6,254,593 B1 | 7/2001 | Wilson |
| 6,254,632 B1 | 7/2001 | Wu et al. |
| 6,258,073 B1 | 7/2001 | Mauch |
| 6,258,114 B1 | 7/2001 | Konya et al. |
| 6,258,116 B1 | 7/2001 | Hojeibane |
| 6,261,316 B1 | 7/2001 | Shaolian et al. |
| 6,261,317 B1 | 7/2001 | Inoue |
| 6,264,662 B1 | 7/2001 | Lauterjung |
| 6,264,684 B1 | 7/2001 | Banas et al. |
| 6,267,783 B1 | 7/2001 | Letendre et al. |
| 6,267,834 B1 | 7/2001 | Shannon et al. |
| 6,270,524 B1 | 8/2001 | Kim |
| 6,270,525 B1 | 8/2001 | Letendre et al. |
| 6,270,707 B1 | 8/2001 | Hon et al. |
| 6,273,909 B1 | 8/2001 | Kugler et al. |
| 6,273,910 B1 | 8/2001 | Limon |
| 6,273,911 B1 | 8/2001 | Cox et al. |
| 6,280,457 B1 | 8/2001 | Wallace et al. |
| 6,280,466 B1 | 8/2001 | Kugler et al. |
| 6,280,467 B1 | 8/2001 | Leonhardt et al. |
| 6,283,991 B1 | 9/2001 | Cox et al. |
| 6,287,315 B1 | 9/2001 | Wijeratne et al. |
| 6,287,329 B1 | 9/2001 | Duarig et al. |
| 6,287,330 B1 | 9/2001 | Johansson et al. |
| 6,287,335 B1 | 9/2001 | Drasler et al. |
| 6,287,336 B1 | 9/2001 | Globerman et al. |
| 6,290,728 B1 | 9/2001 | Phelps et al. |
| 6,293,966 B1 * | 9/2001 | Frantzen ............... 623/1.15 |
| 6,293,968 B1 | 9/2001 | Taheri |
| 6,293,969 B1 | 9/2001 | Chuter |
| 6,296,661 B1 | 10/2001 | Davila et al. |
| 6,302,891 B1 | 10/2001 | Nadal |
| 6,302,905 B1 | 10/2001 | Goldsteen et al. |
| 6,302,906 B1 | 10/2001 | Goicoechea et al. |
| 6,302,908 B1 | 10/2001 | Parodi |
| 6,303,100 B1 | 10/2001 | Ricci et al. |
| 6,306,141 B1 | 10/2001 | Jervis |
| 6,306,145 B1 | 10/2001 | Laschinsky |
| 6,306,164 B1 | 10/2001 | Kujawski |
| 6,306,165 B1 | 10/2001 | Patnaik et al. |
| 6,312,458 B1 | 11/2001 | Golds |
| 6,312,460 B2 | 11/2001 | Drasler et al. |
| 6,312,462 B1 | 11/2001 | McDermott et al. |
| 6,315,791 B1 | 11/2001 | Gingras et al. |
| 6,319,276 B1 | 11/2001 | Holman et al. |
| 6,319,278 B1 | 11/2001 | Quinn |
| 6,319,279 B1 | 11/2001 | Shannon et al. |
| 6,322,587 B1 | 11/2001 | Quiachon et al. |
| 6,325,819 B1 | 12/2001 | Pavcnik et al. |
| 6,325,823 B1 | 12/2001 | Horzewski et al. |
| 6,325,824 B2 | 12/2001 | Limon |
| 6,325,825 B1 | 12/2001 | Kula et al. |
| 6,328,762 B1 | 12/2001 | Anderson et al. |
| 6,331,186 B1 | 12/2001 | Wang et al. |
| 6,331,188 B1 | 12/2001 | Lau et al. |
| 6,331,190 B1 | 12/2001 | Shokoohi et al. |
| 6,331,191 B1 | 12/2001 | Chobotov |
| 6,334,869 B1 | 1/2002 | Leonhardt et al. |
| 6,336,937 B1 | 1/2002 | Vonesh et al. |
| 6,344,044 B1 | 2/2002 | Fulkerson et al. |
| 6,344,054 B1 | 2/2002 | Parodi |
| 6,344,055 B1 | 2/2002 | Shukov |
| 6,346,118 B1 | 2/2002 | Baker et al. |
| 6,346,119 B1 | 2/2002 | Kuwahara et al. |
| 6,348,065 B1 | 2/2002 | Brown et al. |
| 6,350,277 B1 | 2/2002 | Kocur |
| 6,352,553 B1 | 3/2002 | Van der Burg et al. |
| 6,352,561 B1 | 3/2002 | Leopold et al. |
| 6,355,055 B1 | 3/2002 | Waksman et al. |
| 6,355,056 B1 | 3/2002 | Pnheiro |
| 6,355,060 B1 | 3/2002 | Lenker et al. |
| 6,355,063 B1 | 3/2002 | Calcote |
| 6,357,104 B1 | 3/2002 | Myers |
| 6,358,276 B1 | 3/2002 | Edwin et al. |
| 6,358,284 B1 | 3/2002 | Fearnot et al. |
| 6,361,637 B2 | 3/2002 | Martin et al. |
| 6,363,938 B2 | 4/2002 | Saadat |
| 6,364,856 B1 | 4/2002 | Ding et al. |
| 6,364,904 B1 | 4/2002 | Smith |
| 6,368,346 B1 | 4/2002 | Jadhav |
| 6,368,347 B1 | 4/2002 | Maini et al. |
| 6,368,355 B1 | 4/2002 | Uflacker |
| 6,371,979 B1 | 4/2002 | Beyar et al. |
| 6,372,136 B1 | 4/2002 | Nakatsuka |
| 6,375,787 B1 | 4/2002 | Lukic |
| 6,379,381 B1 | 4/2002 | Hossainy et al. |
| 6,379,382 B1 | 4/2002 | Yang |
| 6,379,392 B1 | 4/2002 | Walak |
| 6,383,213 B2 | 5/2002 | Wilson et al. |
| 6,383,214 B1 | 5/2002 | Banas et al. |
| 6,387,119 B2 | 5/2002 | Wolf et al. |
| 6,387,124 B1 | 5/2002 | Buscemi et al. |
| 6,391,050 B1 | 5/2002 | Broome |
| 6,391,052 B2 | 5/2002 | Buirge et al. |
| 6,395,019 B2 | 5/2002 | Chobotov |
| 6,395,022 B1 | 5/2002 | Piplani et al. |
| 6,395,208 B1 | 5/2002 | Herweck et al. |
| 6,398,803 B1 | 6/2002 | Layne et al. |
| 6,402,779 B1 | 6/2002 | Colone et al. |
| 6,406,489 B1 | 6/2002 | Richter et al. |
| 6,409,749 B1 | 6/2002 | Maynard |
| 6,409,750 B1 | 6/2002 | Hyodoh |
| 6,409,754 B1 | 6/2002 | Smith et al. |
| 6,409,756 B1 | 6/2002 | Murphy |
| 6,409,757 B1 | 6/2002 | Trout et al. |
| 6,409,761 B1 | 6/2002 | Jang |
| 6,413,269 B1 | 7/2002 | Bui et al. |
| 6,416,535 B1 | 7/2002 | Lazarus |
| 6,416,536 B1 | 7/2002 | Yee |
| 6,416,537 B1 | 7/2002 | Martakos et al. |
| 6,416,538 B1 | 7/2002 | Ley et al. |
| 6,416,539 B1 | 7/2002 | Hassdenteufel |
| 6,416,542 B1 | 7/2002 | Marcade et al. |
| 6,419,701 B1 | 7/2002 | Cook et al. |
| 6,423,084 B1 | 7/2002 | St. Germain |
| 6,423,089 B1 | 7/2002 | Gingras et al. |
| 6,423,090 B1 | 7/2002 | Hancock |
| 6,425,855 B2 | 7/2002 | Tomonto |
| 6,425,898 B1 | 7/2002 | Wilson et al. |
| 6,428,506 B1 | 8/2002 | Simhambhatla et al. |
| 6,428,565 B1 | 8/2002 | Wisselink |
| 6,428,566 B1 | 8/2002 | Holt |
| 6,428,567 B1 | 8/2002 | Wilson et al. |
| 6,428,569 B1 | 8/2002 | Brown |
| 6,428,570 B1 | 8/2002 | Globerman |
| 6,428,571 B1 | 8/2002 | Lentz et al. |
| 6,432,129 B2 | 8/2002 | DiCaprio |
| 6,432,131 B1 | 8/2002 | Ravenscroft |
| 6,432,132 B1 | 8/2002 | Cottone et al. |
| 6,436,104 B2 | 8/2002 | Hoieibane |
| 6,436,133 B1 | 8/2002 | Furst et al. |
| 6,436,134 B2 | 8/2002 | Richter et al. |
| 6,436,135 B1 | 8/2002 | Goldfarb |
| 6,440,165 B1 | 8/2002 | Richter et al. |
| 6,443,941 B1 | 9/2002 | Slepian et al. |

| | | |
|---|---|---|
| 6,443,979 B1 | 9/2002 | Stalker et al. |
| 6,443,981 B1 | 9/2002 | Colone et al. |
| 6,447,501 B1 | 9/2002 | Solar et al. |
| 6,447,522 B2 | 9/2002 | Gambale et al. |
| 6,451,047 B2 | 9/2002 | McCrea et al. |
| 6,451,050 B1 | 9/2002 | Rudakov et al. |
| 6,451,053 B1 | 9/2002 | Dehdashtian et al. |
| 6,454,796 B1 | 9/2002 | Barkman et al. |
| 6,461,381 B2 | 10/2002 | Israel et al. |
| 6,464,720 B2 | 10/2002 | Boatman et al. |
| 6,464,721 B1 | 10/2002 | Marcade et al. |
| 6,464,722 B2 | 10/2002 | Israel et al. |
| 6,471,718 B1 | 10/2002 | Staehle et al. |
| 6,471,720 B1 | 10/2002 | Ehr et al. |
| 6,471,721 B1 | 10/2002 | Dang |
| 6,471,722 B1 | 10/2002 | Inoue |
| 6,475,166 B1 | 11/2002 | Escano |
| 6,475,208 B2 | 11/2002 | Mauch |
| 6,475,236 B1 | 11/2002 | Roubin et al. |
| 6,475,237 B2 | 11/2002 | Drasler |
| 6,475,238 B1 | 11/2002 | Fedida |
| 6,475,466 B1 | 11/2002 | Ricci et al. |
| 6,478,807 B1 | 11/2002 | Foreman et al. |
| 6,478,815 B1 | 11/2002 | Alt |
| 6,478,816 B1 | 11/2002 | Kveen et al. |
| 6,482,227 B1 | 11/2002 | Solovay |
| 6,485,507 B1 | 11/2002 | Walak et al. |
| 6,485,508 B1 | 11/2002 | McGuinness |
| 6,485,509 B2 | 11/2002 | Killion et al. |
| 6,485,511 B2 | 11/2002 | Lau et al. |
| 6,485,513 B1 | 11/2002 | Fan |
| 6,485,515 B2 | 11/2002 | Strecker |
| 6,485,524 B2 | 11/2002 | Strecker |
| 6,488,694 B1 | 12/2002 | Lau et al. |
| 6,488,700 B2 | 12/2002 | Klumb et al. |
| 6,488,701 B1 | 12/2002 | Nolting et al. |
| 6,488,705 B2 | 12/2002 | Schmitt et al. |
| 6,491,718 B1 | 12/2002 | Ahmad |
| 6,491,719 B1 | 12/2002 | Fogary et al. |
| 6,494,875 B1 | 12/2002 | Mauch |
| 6,494,904 B1 | 12/2002 | Love |
| 6,494,907 B1 | 12/2002 | Bulver |
| 6,494,909 B2 | 12/2002 | Greenhalgh |
| 6,497,722 B1 | 12/2002 | Von Oepen et al. |
| 6,497,723 B1 | 12/2002 | Starck et al. |
| 6,500,202 B1 | 12/2002 | Shaolian et al. |
| 6,500,203 B1 | 12/2002 | Thompson et al. |
| 6,500,204 B1 | 12/2002 | Igaki |
| 6,500,532 B1 | 12/2002 | Ruefer et al. |
| 6,503,271 B2 | 1/2003 | Duerig et al. |
| 6,506,211 B1 | 1/2003 | Doran et al. |
| 6,508,833 B2 | 1/2003 | Pavcnik et al. |
| 6,508,834 B1 | 1/2003 | Pinchasik et al. |
| 6,514,281 B1 | 2/2003 | Blaeser et al. |
| 6,517,558 B2 | 2/2003 | Gittings et al. |
| 6,517,571 B1 | 2/2003 | Brauker et al. |
| 6,517,573 B1 | 2/2003 | Pollock et al. |
| 6,517,574 B1 | 2/2003 | Chuter |
| 6,520,983 B1 | 2/2003 | Colgan et al. |
| 6,520,984 B1 | 2/2003 | Garrison et al. |
| 6,520,986 B2 | 2/2003 | Martin et al. |
| 6,524,334 B1 | 2/2003 | Thompson |
| 6,524,335 B1 | 2/2003 | Hartley et al. |
| 6,524,336 B1 | 2/2003 | Papazolgou et al. |
| 6,530,765 B1 | 3/2003 | Zdrahala et al. |
| 6,530,947 B1 | 3/2003 | Euteneuer et al. |
| 6,530,950 B1 | 3/2003 | Alvarado et al. |
| 6,533,806 B1 | 3/2003 | Sullivan et al. |
| 6,533,807 B2 | 3/2003 | Wolinsky et al. |
| 6,533,808 B1 | 3/2003 | Thompson et al. |
| 6,533,811 B1 | 3/2003 | Ryan et al. |
| 6,537,202 B1 | 3/2003 | Frantzen |
| 6,540,778 B1 | 4/2003 | Quiachon et al. |
| 6,540,780 B1 | 4/2003 | Zilla et al. |
| 6,547,813 B2 | 4/2003 | Stiger et al. |
| 6,547,814 B2 | 4/2003 | Edwin et al. |
| 6,547,815 B2 | 4/2003 | Myers |
| 6,547,817 B1 | 4/2003 | Fischell et al. |
| 6,548,013 B2 | 4/2003 | Kadavy et al. |
| 6,551,350 B1 | 4/2003 | Thornton et al. |
| 6,554,857 B1 | 4/2003 | Zilla et al. |
| 6,554,858 B2 | 4/2003 | Dereume et al. |
| 6,558,414 B2 | 5/2003 | Layne |
| 6,558,415 B2 | 5/2003 | Thompson |
| 6,562,063 B1 | 5/2003 | Euteneuer et al. |
| 6,565,597 B1 | 5/2003 | Fearnot |
| 6,569,150 B2 | 5/2003 | Teague |
| 6,569,190 B2 | 5/2003 | Whalen, II et al. |
| 6,569,193 B1 | 5/2003 | Cox et al. |
| 6,572,649 B1 | 6/2003 | Berry et al. |
| 6,575,994 B1 | 6/2003 | Marin |
| 6,576,009 B2 | 6/2003 | Ryan et al. |
| 6,579,314 B1 | 6/2003 | Lombardi et al. |
| 6,582,458 B1 | 6/2003 | White et al. |
| 6,589,274 B2 | 7/2003 | Stiger et al. |
| 6,589,275 B1 | 7/2003 | Ivancev et al. |
| 6,592,614 B2 | 7/2003 | Lenker et al. |
| 6,602,269 B2 | 8/2003 | Wallace et al. |
| 6,602,280 B2 * | 8/2003 | Chobotov .................... 623/1.11 |
| 6,602,283 B2 | 8/2003 | Doran et al. |
| 6,605,110 B2 | 8/2003 | Harrison |
| 6,607,551 B1 | 8/2003 | Sullivan et al. |
| 6,613,082 B2 | 9/2003 | Yang |
| 6,613,083 B2 | 9/2003 | Alt |
| 6,613,084 B2 | 9/2003 | Yang |
| 6,620,190 B1 | 9/2003 | Colone |
| 6,626,938 B1 | 9/2003 | Butaric et al. |
| 6,635,079 B2 | 10/2003 | Unsworth et al. |
| 6,645,240 B2 | 11/2003 | Yee |
| 6,652,554 B1 | 11/2003 | Wholey et al. |
| 6,652,570 B2 | 11/2003 | Smith et al. |
| 6,652,573 B2 | 11/2003 | Oepen |
| 6,652,575 B2 | 11/2003 | Wang |
| 6,652,580 B1 | 11/2003 | Chutter |
| 6,676,667 B2 | 11/2003 | Mareiro et al. |
| 6,656,215 B1 | 12/2003 | Yanez et al. |
| 6,656,506 B1 | 12/2003 | Wu et al. |
| 6,660,030 B2 | 12/2003 | Shaolian et al. |
| 6,663,662 B2 | 12/2003 | Pacetti et al. |
| 6,663,663 B2 | 12/2003 | Kim et al. |
| 6,663,665 B2 | 12/2003 | Shaolian et al. |
| 6,663,667 B2 | 12/2003 | Dehdashtian et al. |
| 6,669,720 B1 | 12/2003 | Pierce |
| 6,669,723 B2 | 12/2003 | Killion et al. |
| 6,669,724 B2 | 12/2003 | Park et al. |
| 6,673,102 B1 | 1/2004 | Vonesh et al. |
| 6,673,103 B1 | 1/2004 | Golds et al. |
| 6,673,106 B2 | 1/2004 | Mitelberg et al. |
| 6,673,107 B1 | 1/2004 | Brandt et al. |
| 6,676,695 B2 | 1/2004 | Solem |
| 6,679,911 B2 | 1/2004 | Burgermeister |
| 6,685,736 B1 | 2/2004 | White et al. |
| 6,689,158 B1 | 2/2004 | White et al. |
| 6,689,159 B2 | 2/2004 | Hartigan et al. |
| 6,692,523 B2 | 2/2004 | Holman et al. |
| 6,694,983 B2 | 2/2004 | Hall et al. |
| 6,695,833 B1 | 2/2004 | Frantzen |
| 6,695,875 B2 | 2/2004 | Stelter et al. |
| 6,695,877 B2 | 2/2004 | Brucker et al. |
| 6,696,666 B2 | 2/2004 | Merdan et al. |
| 6,699,274 B2 | 3/2004 | Stinson |
| 6,699,277 B1 | 3/2004 | Freidberg et al. |
| 6,702,847 B2 | 3/2004 | DiCarlo |
| 6,702,849 B1 | 3/2004 | Dutta et al. |
| 6,706,064 B1 | 3/2004 | Anson |
| 6,709,449 B2 | 3/2004 | Camrud et al. |
| 6,709,455 B1 | 3/2004 | Chouinard |
| 6,712,827 B2 | 3/2004 | Ellis et al. |
| 6,716,238 B2 | 4/2004 | Elliott |
| 6,716,239 B2 | 4/2004 | Sowinski |
| 6,719,783 B2 | 4/2004 | Lentz et al. |
| 6,726,712 B1 | 4/2004 | Raeder-Devens |
| 6,730,119 B1 | 5/2004 | Smalling |
| 6,733,521 B2 | 5/2004 | Chobotov et al. |
| 6,736,839 B2 | 5/2004 | Cummings |
| 6,740,111 B1 | 5/2004 | Lauterjung |
| 6,740,114 B2 | 5/2004 | Burgermeister |
| 6,740,115 B2 | 5/2004 | Lombardi |

| | | | | | | |
|---|---|---|---|---|---|---|
| 6,743,210 B2 | 6/2004 | Hart et al. | 7,094,255 B2 | 8/2006 | Penn et al. | |
| 6,743,511 B2 | 6/2004 | Dittrich et al. | 7,108,715 B2 | 9/2006 | Brown et al. | |
| 6,746,890 B2 | 6/2004 | Gupta | 7,115,140 B2 | 10/2006 | Stoltze et al. | |
| 6,752,829 B2 | 6/2004 | Kocur et al. | 7,125,464 B2 | 10/2006 | Chobotov et al. | |
| 6,755,855 B2 | 6/2004 | Yurek et al. | 7,128,754 B2 | 10/2006 | Bolduc | |
| 6,758,858 B2 | 7/2004 | McCrea et al. | 7,128,755 B2 | 10/2006 | Su et al. | |
| 6,761,733 B2 | 7/2004 | Chobotov et al. | 7,147,455 B2 | 12/2006 | Chobotov et al. | |
| 6,770,086 B1 | 8/2004 | Girton et al. | 7,147,660 B2 * | 12/2006 | Chobotov et al. | 623/1.14 |
| 6,770,087 B2 | 8/2004 | Layne et al. | 7,147,661 B2 | 12/2006 | Chobotov et al. | |
| 6,773,453 B2 | 8/2004 | Ravenscroft | 7,150,758 B2 | 12/2006 | Kari et al. | |
| 6,773,457 B2 | 8/2004 | Gellman et al. | 7,160,318 B2 | 1/2007 | Greenberg et al. | |
| 6,776,604 B1 | 8/2004 | Chobotov et al. | 7,175,651 B2 | 2/2007 | Kerr | |
| 6,776,793 B2 | 8/2004 | Brown et al. | 7,175,652 B2 | 2/2007 | Cook et al. | |
| 6,786,920 B2 | 9/2004 | Shannon et al. | 7,189,256 B2 | 3/2007 | Smith | |
| 6,790,227 B2 | 9/2004 | Burgermeister | 7,192,441 B2 | 3/2007 | Sherry | |
| 6,790,230 B2 | 9/2004 | Beyersdorf et al. | 7,223,280 B2 | 5/2007 | Anson et al. | |
| 6,793,672 B2 | 9/2004 | Khosravi et al. | 7,226,474 B2 | 6/2007 | Iancea et al. | |
| 6,796,999 B2 | 9/2004 | Pinchasik | 7,229,470 B2 | 6/2007 | Brian et al. | |
| 6,802,849 B2 | 10/2004 | Siaeser et al. | 7,232,459 B2 | 6/2007 | Greenberg | |
| 6,802,856 B2 | 10/2004 | Wilson | 7,244,242 B2 | 7/2007 | Freyman | |
| 6,814,753 B2 | 11/2004 | Schmitt | 7,273,494 B2 | 9/2007 | Rolando et al. | |
| 6,818,013 B2 | 11/2004 | Mitelberg et al. | 7,284,399 B1 | 10/2007 | Sisco | |
| 6,821,292 B2 | 11/2004 | Pazienza et al. | 7,294,147 B2 | 11/2007 | Hartley | |
| 6,824,558 B2 | 11/2004 | Parodi | 7,314,484 B2 | 1/2008 | Deem et al. | |
| 6,827,726 B2 | 12/2004 | Parodi | 7,338,518 B2 | 3/2008 | Chobotov | |
| 6,827,731 B2 | 12/2004 | Annstrong et al. | 7,351,256 B2 | 4/2008 | Hojeibane et al. | |
| 6,827,735 B2 | 12/2004 | Greenbeg | 7,425,219 B2 | 9/2008 | Quadri | |
| 6,827,737 B2 | 12/2004 | Hill et al. | 7,452,374 B2 | 10/2008 | Hain et al. | |
| 6,833,004 B2 | 12/2004 | Ishil et al. | 7,465,270 B2 | 12/2008 | Li | |
| 6,841,213 B2 | 1/2005 | Parsonage et al. | 7,485,138 B2 | 2/2009 | Fearnot et al. | |
| 6,843,802 B1 | 1/2005 | Villalobos et al. | 7,491,230 B2 | 2/2009 | Holman et al. | |
| 6,849,086 B2 | 2/2005 | Cragg | 7,491,234 B2 | 2/2009 | Palasis et al. | |
| 6,858,035 B2 | 2/2005 | Whayne | 7,500,988 B1 | 3/2009 | Butaric et al. | |
| 6,860,900 B2 | 3/2005 | Clerc et al. | 7,510,571 B2 | 3/2009 | Spiridigliozzi et al. | |
| 6,863,685 B2 | 3/2005 | Davila et al. | 7,520,890 B2 | 4/2009 | Phillips | |
| 6,869,443 B2 | 3/2005 | Buscemi et al. | 7,520,895 B2 | 4/2009 | Douglas et al. | |
| 6,878,160 B2 | 4/2005 | Gilligan et al. | 7,530,988 B2 | 5/2009 | Evans et al. | |
| 6,878,161 B2 | 4/2005 | Lenker | 7,550,004 B2 | 6/2009 | Bahaler et al. | |
| 6,884,260 B2 | 4/2005 | Kugler et al. | 7,550,005 B2 | 6/2009 | Bates et al. | |
| 6,899,728 B1 | 5/2005 | Philips et al. | 7,556,645 B2 | 7/2009 | Lashinski et al. | |
| 6,918,925 B2 | 7/2005 | Tehrani | 7,591,843 B1 | 9/2009 | Escano | |
| 6,918,927 B2 | 7/2005 | Bates et al. | 7,597,710 B2 | 10/2009 | Obermiller | |
| 6,923,827 B2 | 8/2005 | Campbell et al. | 2001/0014794 A1 | 8/2001 | Moll | |
| 6,926,732 B2 | 8/2005 | Derus et al. | 2001/0029349 A1 | 10/2001 | Leschinsky | |
| 6,929,659 B2 | 8/2005 | Pinchuk | 2001/0039445 A1 | 11/2001 | Hall et al. | |
| 6,929,709 B2 | 8/2005 | Smith | 2001/0041928 A1 | 11/2001 | Pavcnik et al. | |
| 6,939,370 B2 | 9/2005 | Hartley et al. | 2001/0044652 A1 | 11/2001 | Moore | |
| 6,939,374 B2 | 9/2005 | Banik et al. | 2001/0049534 A1 | 12/2001 | Lachat | |
| 6,942,689 B2 | 9/2005 | Majercak | 2002/0007193 A1 | 1/2002 | Tanner et al. | |
| 6,945,989 B1 | 9/2005 | Betelia et al. | 2002/0011684 A1 | 1/2002 | Bahar et al. | |
| 6,945,992 B2 * | 9/2005 | Goodson et al. ............ 623/1.13 | 2002/0016626 A1 | 2/2002 | DiMatteo et al. | |
| 6,949,120 B2 | 9/2005 | Kveen et al. | 2002/0019659 A1 | 2/2002 | Goicoechea et al. | |
| 6,962,602 B2 | 11/2005 | Vardi et al. | 2002/0029051 A1 | 3/2002 | Callister et al. | |
| 6,962,603 B1 | 11/2005 | Brown | 2002/0032408 A1 | 3/2002 | Parker et al. | |
| 6,964,677 B2 | 11/2005 | Osypka | 2002/0040236 A1 | 4/2002 | Lau et al. | |
| 6,974,471 B2 | 12/2005 | Van Schie et al. | 2002/0040237 A1 | 4/2002 | Lentz et al. | |
| 6,974,472 B2 | 12/2005 | Hong et al. | 2002/0042644 A1 | 4/2002 | Greenhalgh | |
| 6,981,982 B2 | 1/2006 | Armstrong et al. | 2002/0045931 A1 | 4/2002 | Sogard et al. | |
| 6,989,026 B2 | 1/2006 | Richter et al. | 2002/0045933 A1 | 4/2002 | Jang | |
| 6,994,722 B2 | 2/2006 | DiCarlo | 2002/0045934 A1 | 4/2002 | Jang | |
| 6,997,945 B2 | 2/2006 | Germain | 2002/0045935 A1 | 4/2002 | Jang | |
| 6,998,060 B2 | 2/2006 | Tomonto | 2002/0049487 A1 | 4/2002 | Lootz et al. | |
| 7,001,407 B2 | 2/2006 | Hansen et al. | 2002/0049490 A1 | 4/2002 | Pollock et al. | |
| 7,001,419 B2 | 2/2006 | DiCaprio et al. | 2002/0049493 A1 | 4/2002 | Jang | |
| 7,001,431 B2 | 2/2006 | Bao et al. | 2002/0052627 A1 | 5/2002 | Boylan et al. | |
| 7,011,673 B2 | 3/2006 | Fischell et al. | 2002/0052644 A1 * | 5/2002 | Shaolian et al. ............ 623/1.13 |
| 7,011,674 B2 | 3/2006 | Brenneman | 2002/0052649 A1 | 5/2002 | Greenhalgh | |
| 7,022,132 B2 | 4/2006 | Kocur | 2002/0055768 A1 | 5/2002 | Hess et al. | |
| 7,022,135 B2 | 4/2006 | Zilla et al. | 2002/0065552 A1 | 5/2002 | Jayaraman et al. | |
| 7,033,389 B2 | 4/2006 | Sherry | 2002/0072792 A1 | 6/2002 | Burgermeister et al. | |
| 7,056,325 B1 | 6/2006 | Makower | 2002/0072793 A1 | 6/2002 | Rolando et al. | |
| 7,056,336 B2 | 6/2006 | Armstrong et al. | 2002/0076542 A1 | 6/2002 | Kramer et al. | |
| 7,056,412 B2 | 6/2006 | Henderson | 2002/0077692 A1 | 6/2002 | Besselink | |
| 7,066,951 B2 | 6/2006 | Chobotov | 2002/0082680 A1 | 6/2002 | Stanley et al. | |
| 7,073,504 B2 | 7/2006 | Callister et al. | 2002/0082682 A1 | 6/2002 | Barclay et al. | |
| 7,081,129 B2 | 7/2006 | Chobotov | 2002/0082685 A1 | 6/2002 | Sirhan et al. | |
| 7,081,132 B2 | 7/2006 | Cook et al. | 2002/0095208 A1 | 7/2002 | Gregorich et al. | |
| 7,083,642 B2 | 8/2006 | Sirhan et al. | 2002/0096252 A1 | 7/2002 | Lukic | |
| 7,090,693 B1 | 8/2006 | Chobotov et al. | 2002/0107561 A1 | 8/2002 | Pinheiro | |

| | | |
|---|---|---|
| 2002/0120321 A1 | 8/2002 | Gunderson et al. |
| 2002/0120327 A1 | 8/2002 | Cox et al. |
| 2002/0123790 A1 | 9/2002 | White et al. |
| 2002/0123791 A1 | 9/2002 | Harrison |
| 2002/0123796 A1 | 9/2002 | Majercak et al. |
| 2002/0143387 A1 | 10/2002 | Soetikno et al. |
| 2002/0147492 A1 | 10/2002 | Shokoohi et al. |
| 2002/0151953 A1 | 10/2002 | Chobotov et al. |
| 2002/0161376 A1 | 10/2002 | Barry et al. |
| 2002/0165603 A1 | 11/2002 | Thornton et al. |
| 2002/0169497 A1 | 11/2002 | Wholey et al. |
| 2002/0183826 A1 | 12/2002 | Dorn et al. |
| 2002/0183827 A1 | 12/2002 | Derus et al. |
| 2002/0188346 A1 | 12/2002 | Healy et al. |
| 2002/0188347 A1 | 12/2002 | Mathis |
| 2002/0193867 A1 | 12/2002 | Gladdish, Jr. et al. |
| 2002/0193872 A1 | 12/2002 | Trout et al. |
| 2002/0193873 A1 | 12/2002 | Brucker et al. |
| 2002/0198585 A1 | 12/2002 | Wisselink |
| 2002/0198587 A1 | 12/2002 | Greenberg et al. |
| 2003/0004560 A1* | 1/2003 | Chobotov et al. ............ 623/1.11 |
| 2003/0004565 A1 | 1/2003 | Harnek et al. |
| 2003/0009212 A1 | 1/2003 | Kerr |
| 2003/0014075 A1 | 1/2003 | Rosenbluth et al. |
| 2003/0040803 A1 | 2/2003 | Rioux et al. |
| 2003/0050684 A1 | 3/2003 | Abrams et al. |
| 2003/0068296 A1 | 4/2003 | Ricci et al. |
| 2003/0083736 A1 | 5/2003 | Brown et al. |
| 2003/0097170 A1 | 5/2003 | Friedrich et al. |
| 2003/0120263 A1 | 6/2003 | Ouriel et al. |
| 2003/0120331 A1 | 6/2003 | Chobotov et al. |
| 2003/0125797 A1 | 7/2003 | Chobotov |
| 2003/0135256 A1 | 7/2003 | Gallagher et al. |
| 2003/0135261 A1 | 7/2003 | Kugler et al. |
| 2003/0176912 A1 | 9/2003 | Chuter et al. |
| 2003/0191518 A1 | 10/2003 | Spiridigliozzi et al. |
| 2003/0204236 A1 | 10/2003 | Letort |
| 2003/0204244 A1 | 10/2003 | Stiger |
| 2003/0220683 A1 | 11/2003 | Minasian |
| 2003/0225453 A1 | 12/2003 | Murch |
| 2004/0024446 A1 | 2/2004 | Smith |
| 2004/0034407 A1 | 2/2004 | Sherry |
| 2004/0044395 A1 | 3/2004 | Nelson |
| 2004/0049212 A1 | 3/2004 | Whayne |
| 2004/0049264 A1 | 3/2004 | Sowinski et al. |
| 2004/0093055 A1 | 5/2004 | Bartorelli et al. |
| 2004/0093064 A1 | 5/2004 | Bosma |
| 2004/0093068 A1 | 5/2004 | Bergen et al. |
| 2004/0093078 A1 | 5/2004 | Moll et al. |
| 2004/0098096 A1 | 5/2004 | Eton |
| 2004/0106974 A1 | 6/2004 | Greenberg et al. |
| 2004/0116997 A1 | 6/2004 | Taylor et al. |
| 2004/0138734 A1 | 7/2004 | Chobotov et al. |
| 2004/0162607 A1 | 8/2004 | Masroor |
| 2004/0167614 A1 | 8/2004 | Anson |
| 2004/0210304 A1 | 10/2004 | Seguin et al. |
| 2004/0215213 A1 | 10/2004 | Dolan |
| 2004/0220664 A1 | 11/2004 | Chobotov |
| 2004/0254625 A1 | 12/2004 | Stephens |
| 2005/0033406 A1* | 2/2005 | Barnhart et al. ............ 623/1.13 |
| 2005/0049691 A1 | 3/2005 | Mercile et al. |
| 2005/0075715 A1 | 4/2005 | Borges et al. |
| 2005/0090804 A1 | 4/2005 | Chobotov et al. |
| 2005/0090901 A1 | 4/2005 | Studer |
| 2005/0158272 A1 | 7/2005 | Whirley et al. |
| 2005/0171593 A1 | 8/2005 | Whirley et al. |
| 2005/0177222 A1 | 8/2005 | Mead |
| 2005/0222669 A1 | 10/2005 | Purdy |
| 2005/0228484 A1 | 10/2005 | Stephens et al. |
| 2006/0009833 A1 | 1/2006 | Chobotov et al. |
| 2006/0020319 A1 | 1/2006 | Kim et al. |
| 2006/0079952 A1 | 4/2006 | Kaplan et al. |
| 2006/0136047 A1 | 6/2006 | Obermiller et al. |
| 2006/0149364 A1 | 7/2006 | Walak et al. |
| 2006/0178732 A1 | 8/2006 | Chobotov et al. |
| 2006/0186143 A1 | 8/2006 | Argentine |
| 2006/0212112 A1 | 9/2006 | Evans et al. |
| 2006/0224232 A1 | 10/2006 | Chobotov |
| 2006/0233990 A1 | 10/2006 | Humphrey et al. |
| 2006/0233991 A1 | 10/2006 | Humphrey et al. |
| 2006/0287713 A1 | 12/2006 | Douglas et al. |
| 2006/0292206 A1 | 12/2006 | Kim et al. |
| 2007/0012396 A1 | 1/2007 | Chobotov et al. |
| 2007/0016281 A1 | 1/2007 | Melsheimer |
| 2007/0055347 A1 | 3/2007 | Arbeferize |
| 2007/0112413 A1 | 5/2007 | Smith |
| 2007/0162106 A1 | 7/2007 | Evans et al. |
| 2007/0167901 A1 | 7/2007 | Herrig et al. |
| 2007/0203571 A1 | 8/2007 | Kaplan et al. |
| 2007/0219627 A1 | 9/2007 | Chu et al. |
| 2007/0239273 A1 | 10/2007 | Allen |
| 2007/0244539 A1 | 10/2007 | Lentz et al. |
| 2007/0276477 A1 | 11/2007 | Lee et al. |
| 2007/0282369 A1 | 12/2007 | Gilson et al. |
| 2008/0015687 A1 | 1/2008 | Clarke et al. |
| 2008/0027529 A1 | 1/2008 | Hartley et al. |
| 2008/0051705 A1 | 2/2008 | Von Oepen et al. |
| 2008/0058920 A1 | 3/2008 | Kari |
| 2008/0114441 A1 | 5/2008 | Rust |
| 2008/0114442 A1 | 5/2008 | Mitchell et al. |
| 2008/0114443 A1 | 5/2008 | Mitchell |
| 2008/0115678 A1 | 5/2008 | Weinberg |
| 2008/0172119 A1 | 7/2008 | Yamasaki et al. |
| 2008/0228255 A1 | 9/2008 | Rust |
| 2009/0036971 A1* | 2/2009 | Humphrey et al. .......... 623/1.15 |
| 2009/0042796 A1 | 2/2009 | Wallach et al. |
| 2009/0082841 A1 | 3/2009 | Zacharias et al. |
| 2009/0082842 A1 | 3/2009 | Glynn |
| 2009/0082845 A1* | 3/2009 | Chobotov .................... 623/1.13 |
| 2009/0082846 A1* | 3/2009 | Chobotov .................... 623/1.13 |
| 2009/0082847 A1 | 3/2009 | Zacharias et al. |
| 2009/0099649 A1 | 4/2009 | Chobotov et al. |
| 2009/0132020 A1 | 5/2009 | Watson |
| 2009/0132026 A1 | 5/2009 | Martin et al. |
| 2009/0171431 A1 | 7/2009 | Swanson et al. |
| 2009/0182406 A1 | 7/2009 | Blaeser et al. |
| 2009/0198267 A1 | 8/2009 | Evans et al. |
| 2009/0287145 A1 | 11/2009 | Cragg et al. |
| 2010/0211052 A1 | 8/2010 | Brown et al. |

FOREIGN PATENT DOCUMENTS

| | | |
|---|---|---|
| EP | 0714641 | 6/1996 |
| EP | 0775472 | 5/1997 |
| EP | 0792627 | 9/1997 |
| EP | 0808613 | 11/1997 |
| EP | 0819411 | 1/1998 |
| EP | 0943302 | 9/1999 |
| EP | 0997115 | 5/2000 |
| EP | 0480667 | 4/2001 |
| EP | 1093772 | 4/2001 |
| EP | A 1138280 | 10/2001 |
| EP | 0808140 | 12/2001 |
| EP | 1163991 | 12/2001 |
| EP | 1212991 | 6/2002 |
| EP | 1266636 | 12/2002 |
| EP | 1380270 | 1/2004 |
| EP | 1415617 | 4/2004 |
| JP | 49 042773 | 4/1974 |
| JP | 3109404 | 5/1991 |
| JP | 5161665 | 6/1993 |
| JP | 6100054 | 4/1994 |
| JP | 09117511 | 5/1997 |
| JP | 18-126862 | 6/2006 |
| JP | 18-136382 | 6/2006 |
| RU | 1768154 | 10/1992 |
| RU | 1812980 | 4/1993 |
| RU | 2029527 | 2/1995 |
| SU | 1217402 | 3/1986 |
| SU | 1237201 | 6/1986 |
| SU | 1237202 | 6/1986 |
| SU | 1273077 | 11/1986 |
| SU | 1342511 | 10/1987 |
| SU | 1389778 | 4/1988 |
| SU | 1457921 | 2/1989 |
| SU | 1482714 | 5/1989 |
| SU | 1560134 | 4/1990 |
| SU | 1586718 | 8/1990 |
| SU | 1650127 | 5/1991 |

| | | |
|---|---|---|
| SU | 1732964 | 5/1992 |
| WO | WO 91/00792 | 1/1991 |
| WO | WO 92/22604 | 12/1992 |
| WO | WO 93/13824 | 7/1993 |
| WO | WO 93/19804 | 10/1993 |
| WO | WO 94/03127 | 2/1994 |
| WO | WO 95/03754 | 2/1995 |
| WO | WO 95/09586 | 4/1995 |
| WO | WO 96/14095 | 5/1996 |
| WO | WO 96/14808 | 5/1996 |
| WO | WO 97/07751 | 3/1997 |
| WO | WO 97/29716 | 8/1997 |
| WO | WO 98/06355 | 2/1998 |
| WO | WO 98/38947 | 9/1998 |
| WO | WO 98/41167 | 9/1998 |
| WO | WO 98/44870 | 10/1998 |
| WO | WO 98/44873 | 10/1998 |
| WO | WO 99/00073 | 1/1999 |
| WO | WO 99/26559 | 6/1999 |
| WO | WO 99/38455 | 8/1999 |
| WO | WO 99/43378 | 9/1999 |
| WO | WO 99/43379 | 9/1999 |
| WO | WO 00/10487 | 3/2000 |
| WO | WO 00/13613 | 3/2000 |
| WO | WO 00/42947 | 7/2000 |
| WO | WO 00/42948 | 7/2000 |
| WO | WO 00/44808 | 8/2000 |
| WO | WO 00/51522 | 9/2000 |
| WO | WO 00/67675 | 11/2000 |
| WO | WO 00/71179 | 11/2000 |
| WO | WO 01/05331 | 1/2001 |
| WO | WO 01/08599 | 2/2001 |
| WO | WO 01/15633 | 3/2001 |
| WO | WO 01/21108 | 3/2001 |
| WO | WO 01/30270 | 5/2001 |
| WO | WO 01/41675 | 6/2001 |
| WO | WO 01/56500 | 8/2001 |
| WO | WO 01/56504 | 8/2001 |
| WO | WO 01/58384 | 8/2001 |
| WO | WO 01/58387 | 8/2001 |
| WO | WO 01/66037 | 9/2001 |
| WO | WO 01/67993 | 9/2001 |
| WO | WO 01/74270 | 10/2001 |
| WO | WO 01/82836 | 11/2001 |
| WO | WO 02/36332 | 5/2002 |
| WO | WO 02/41804 | 5/2002 |
| WO | WO 02/078569 | 10/2002 |
| WO | WO 02/083038 | 10/2002 |
| WO | WO 02/100454 | 12/2002 |
| WO | WO 03/022180 | 3/2003 |
| WO | WO 03/053287 | 7/2003 |
| WO | WO 03/094795 | 11/2003 |
| WO | WO 03/094799 | 11/2003 |
| WO | WO 2004/002370 | 1/2004 |
| WO | WO 2004/002371 | 1/2004 |
| WO | WO 2004/017866 | 3/2004 |
| WO | WO 2005086942 A2 * | 9/2005 |
| WO | WO 2009/042796 | 4/2009 |
| WO | WO 2009/086200 | 7/2009 |

OTHER PUBLICATIONS

Blum et al. "Endoluminal stent-grafts for infrarenal abdominal aortic aneurysms" N Engl J Med 336(1):13-20 (1997).

Campbell et al., "Balloon-Artery Interactions During Stent Placement: A Finite Element Analysis Approach to Pressure, Compliance, and Stent Design as Contributors to Vascular Injury"; 1999; American Heart Association; pp. 378-383.

Canero et al., "Optimal stent implantation: three-dimensional evaluation of the mutual position of stent and vessel via intracoronary echocardiography," Computers in Cardiology, 261-264 (Sep. 1999).

Donayre, et al., "Fillable endovascular aneurysm repair", Endovascular Today, p. 64-66, Jan. 2009.

Dumoulin C. et al., "Mechanical behavior modeling of balloon expandable stents." Journal of Biomechanics, vol. 33, No. 11, pp. 1461-1470 (available online: Sep. 8, 2000).

Elger et al. "The Influence of Shape on the Stresses in Model Abdominal Aortic Aneurysms," Transactions of the ASME 326:326-32 (1996).

Ernst "Current therapy for infrarenal aortic aneurysms" N Engl J Med 336(1):58-60 (1997).

Haimovitch, L. and Patierson, N., "Robust growth is forecast for endovascular repair of AAAs," The BBI Newsletter, vol. 26, No. 5, pp. 113-144, (May 2003).

How et al. "Mechanical Properties of Arteries and Arterial Grafts," Chapter 1 of Cardiovascular Biomaterials Hasting, G.W. (ed.) London; New York: Springer-Verlag, 1992 pp. 1-35.

International Search Report and Written Opinion mailed on Mar. 26, 2009 for International Application No. PCT/US2008/07727 filed on Sep. 25, 2008 and published as WO/2009/042796 on Apr. 2, 2009.

Lakshmiraghavan, M. Mechanical Wall Stress in Abdominal Aortic Aneurysm: Towards the Development of a Clinical Tool to Predict Aneurysm Rupture. Submitted to the University of Pittsburgh, vol. 59/09-B of Dissertation Abstracts International p. 4948. 285 pages (1998).

Mandai, S. et al. (1992). "Direct Thrombosis of Aneurysms with Cellulose Acetate Polymer. Part I: Results of Thrombosis in Experimental Aneurysms," J. Neurosurgery 77:497-500.

Mirich et al., "Percutaneously Placed Endovascular Grafts for Aortic Aneurysms: Feasibility Study", Radiology, 170/3:1033-1037 (1989).

Moore et al. "Transfemoral endovascular repair of abdominal aortic aneurysm: results of the North American EVT phase 1 trial" J Vasc Surg 23(4):543-553 (1996).

Mower et al. "Stress Distributions in Vascular Aneurysms: Factors Affecting Risk of Aneurysm Rupture," J. Surgical Research 55:151-61 (1993).

Office Action mailed on: May 29, 2009 for U.S. Appl. No. 11/861,746, filed Sep. 26, 2007 and published as US2009/0082845 on Mar. 26, 2009.

Office Action Response filed on: Oct. 28, 2009 for U.S. Appl. No. 11/861,746, filed Sep. 26, 2007 and published as US2009/0082845 on Mar. 26, 2009.

Parodi "Endovascular repair of abdominal aortic aneurysms and other arterial lesions" J Vasc Surg 21(4):549-557 (1995).

Parodi et al., "Transfemoral intraluminal graft implantation for abdominal aortic aneurysms," Ann. Vasc. Surg., 5(6):491-499 (1991).

Perry, M. D. and Chang, R. T., "Finite Element Analysis of NI-TI Alloy Stent Deployment," Proceedings of the Second International Conference on SMST, Asilomar Conference Center, Pacific Grove CA. USA (1997).

Rogers et al., "Balloon-Artery Interactions During Stent Placement: A finite element analysis approach to pressure, compliance and stent design as contributors to vascular injury", 1999 American Heart Association pp. 378-383.

Stern et al., "Interactive Definition of Endoluminal Aortic Stent Size and Morphology Based on Virtual Angioscopic Rendering of 3D Magnetic Resonance Angiography (MRA)," Cars. Computer Assisted Radiology and Surgery, Proceedings of the International Symposium on Computer Assisted Radiology and Surgery:176-180 (Jun. 1999).

Uflacker, R. and Robinson, J., "Endovascular treatment of abdominal aortic aneurysms: a review," Eur. Radial.,11:739-753 (2001).

Verhagen "Latest AAA Innovations: The Endurant Stent Graft System", Veith Symposium Nov. 17, 2007.

Verhagen, Hence J.M. "Endurant Medtronic Endograft for EVAR: advantages & early experience", Slides from Veith Symposium Presentation Nov. 22, 2008.

Vos, A.F.W. et al., "Endovascular Grafting of Complex Aortic Aneurysms with a modular site Branch Stent Graft System in a Porcine Model", Eur J Vasc Endovasc Surg, May 2004 vol. 27 492-497.

Whitcher, "Simulation of in vivo loading conditions of nitinol vascular stent structures", 1997, Elsevier Science Ltd., pp. 1005-1011.

Whitcher, F., "A Finite Element Treatment of the In-Vivo Loading Conditions of NITI AD Vascular Stent and Graft Structures," Proceedings of the Second International Conference on SMST, Asilomar Conference Center, Pacific Grove. CA, USA (1997).

The AneuRx® Stent Graft System Treatment for AAA brochure, "An Innovative Modular Approach for the Treatment of Abdominal Aortic Aneurysms (AAA)," Medtronic AVE, Inc. 1999.

The AneuRx® Stent Graft Treatment for TAA brochure, "An Endoluminal Solution for the Treatment of Descending Thoracic Aortic Aneurysms," Medtronic, Inc. 1999.

Cooley, Denton A., Surgical Treatment of Aortic Aneurysms (Book), W.B. Saunders Company, West Washington Square, PA (1986).

Volodos, N.L. et al. (1987). "New Balloon Catheter for Dilating Arteries and Installing Prosthesis During Distal Endoprosthetics With Self-Fixing Synthetic Prosthesis," *Thesis of VIII Symposium* (Oct. 8-10, 1987), Abstract Only in English, four pages.

Volodos, N.L. et al. (1986) "Self-Fixing Synthetic Prostheisis for Endoprosthesis of Vessels," Vestnik Khigurgii pp. 123-124, Abstract Only in English.

Volodos, N.L. et al. (1989). "Clinical Experience in Use of Self-Fixing Synthetic Prosthesis for Distal and Intraoperative Endoprosthestics of Aora and Iliac Arteries," Theses of Ixth All-Union Symposium (Oct. 2-3, 1989), Abstract only in English, four pages.

Web page, "Drug Eluting Stents—Why Use Drug Eluting Stents?" Polymer Coatings Division; at: URL http://www.lombardmedlcal.co.uk/lombard/pcde.why.html; Lombard Medical; printed Feb. 1, 2005.

Wisselink, W. et al. (2001). "Clipping of Inferior Mesenteric and Lumbar Arteries via Retroperitoneal Laparo-Endoscopic Approach as a Treatment of Persistent Endoleak" Chapter 18 *In* Endoleaks and Endotension, Veith, F.J. et al. eds. Marcel Dekker, Inc. pp. 211-220.

Bozic et al., "Three-dimensional finite element modeling of a cervical vertebra: An investigation of burst fracture mechanism," J. Spinal Disorders, 7(2):102-110 (Apr. 1994).

International Preliminary Report on Patentability mailed on Mar. 30, 2010 for International Application No. PCT/US2008/07727 filed on Sep. 25, 2008 and published as WO/2009/042796 on Apr. 2, 2009.

Office Action mailed on: Feb. 12, 2010 for U.S. Appl. No. 11/861,746 filed on Sep. 26, 2007 and published as US2009/0082845 on Mar. 26, 2009.

US 6,413,270, 07/2002, Thornton et al. (withdrawn)

\* cited by examiner

SYSTEM AND METHOD OF PIVOTED STENT DEPLOYMENT

BACKGROUND OF THE INVENTION

The present invention relates to a system for the treatment of disorders of the vasculature. More specifically, the invention relates to a system for the treatment of disease or injury that potentially compromises the integrity of a flow conduit in the body. For example, an embodiment of the invention is useful in treating indications in the digestive and reproductive systems as well as indications in the cardiovascular system, including thoracic and abdominal aortic aneurysms, arterial dissections (such as those caused by traumatic injury), etc.

For indications such as abdominal aortic aneurysms, traditional open surgery is still the conventional and most widely-utilized treatment when the aneurysm's size has grown to the point that the risk of aneurysm rupture outweighs the drawbacks of surgery. Surgical repair involves replacement of the section of the vessel where the aneurysm has formed with a graft. An example of a surgical procedure is described by Cooley in Surgical Treatment of Aortic Aneurysms, 1986 (W. B. Saunders Company).

Despite its advantages, however, open surgery is fraught with high morbidity and mortality rates, primarily because of the invasive and complex nature of the procedure. Complications associated with surgery include, for example, the possibility of aneurysm rupture, loss of function related to extended periods of restricted blood flow to the extremities, blood loss, myocardial infarction, congestive heart failure, arrhythmia, and complications associated with the use of general anesthesia and mechanical ventilation systems. In addition, the typical patient in need of aneurysm repair is older and in poor health, facts that significantly increase the likelihood of complications.

Due to the risks and complexities of surgical intervention, various attempts have been made to develop alternative methods for treating such disorders. One such method that has enjoyed some degree of success is the catheter-based delivery of a stent-graft via the femoral arteries to exclude the aneurysm from within the aorta. Illustrative stent-grafts and methods of delivery thereof are described in U.S. Patent Application Publication Nos. 2003/0125797A1, 2004/0138734A1 and U.S. Pat. No. 6,295,019, each of which is incorporated herein in its entirety by reference herein.

SUMMARY OF THE INVENTION

In one aspect, the invention provides a stent-graft system comprising a graft member and a stent having a connection end interconnected with the graft member and a free end opposed thereto. A belt retaining structure is provided at the stent free end. A belt is releasably retained in the belt retaining structure and is configured to constrain the stent free end independent of the stent connection end.

In another aspect, the invention provides a method of securing at least one end of a graft within a vessel. The method comprises: positioning within the vessel a stent-graft comprising a stent and a graft with a connection end of the stent connected to an end of the graft, the stent having a free end opposite the connection end, the stent free end including a belt retaining structure with a belt releasably retained thereabout; deploying the stent connection end within the vessel; repositioning the stent-graft within the vessel; and releasing the belt to deploy the free end of the stent.

Other aspects and advantages of the present invention will be apparent from the detailed description of the invention provided hereinafter.

BRIEF DESCRIPTION OF THE DRAWINGS

The invention is best understood from the following detailed description when read in connection with the accompanying drawings. It is emphasized that, according to common practice, the various features of the drawings are not to scale. On the contrary, the dimensions of the various features are arbitrarily expanded or reduced for clarity. Included in the drawings are the following figures.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

Figure 1:
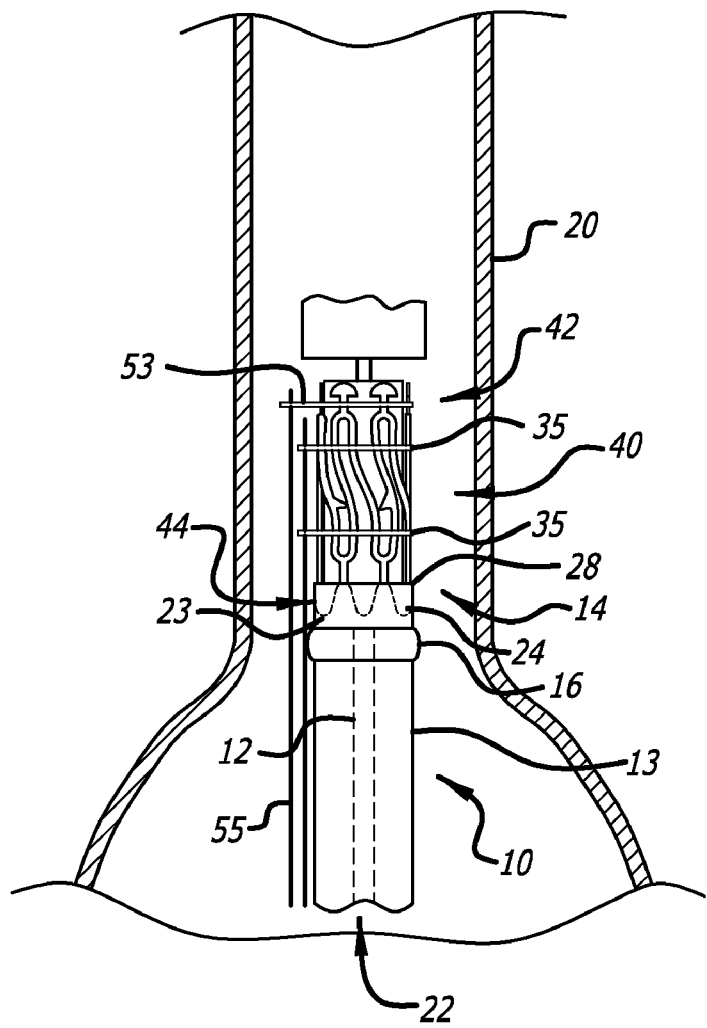
FIG. 1 shows a portion of an endovascular graft according to an embodiment of the present invention in a contracted state for delivery through a catheter.

Referring to FIG. 1, a portion of an illustrative endovascular graft 10 is shown in its contracted configuration. Unless otherwise stated, the term "graft" or "endovascular graft" is used herein to refer to a prosthesis capable of repairing and/or replacing diseased vessels or portions thereof, including generally tubular and bifurcated devices and any components attached or integral thereto. For purposes of illustration, the graft embodiments described herein may be used in the endovascular treatment of abdominal aortic aneurysms (AAA) or thoracic aortic aneurysms, however, other applications are within the scope of the present invention. For the purposes of this application, with reference to endovascular graft devices, the term "proximal" describes the end of the graft that will be oriented towards the oncoming flow of bodily fluid, typically blood, when the device is deployed within a body passageway. The term "distal" therefore describes the graft end opposite the proximal end. Finally, while the drawings in the various figures are accurate representations of the various embodiments of the present invention, the proportions of the various components thereof are not necessarily shown to exact scale within and among or between any given figure(s).

An end of the graft 10 is illustrated and may represent the proximal or distal end of the graft 10. The graft 10 includes a generally tubular structure or graft body section 13 comprised of one or more layers of fusible material, such as expanded polytetrafluoroethylene (ePTFE). An inflatable cuff 16 is disposed at or near the end 14 of graft body section 13. A neck portion 23 is disposed in the vicinity of graft body section end 14 and serves as an additional means to help seal the deployed graft against the inside of a body passageway. Graft body section 13 forms a longitudinal lumen 22 configured to confine a flow of fluid therethrough.

A attachment ring 24 is affixed to or integrally formed in graft body section 13, or as shown in FIG. 1, at or near graft body section end 14 and neck portion 23. In the embodiment of FIG. 1, attachment ring 24 is a serpentine ring structure comprising apices 28. Other embodiments of attachment ring 24 may take different configurations. Attachment ring 24 may be made from any suitable material that permits expansion from a constrained state, most usefully a shape memory alloy having superelastic properties such as nickel titanium (NiTi). Other suitable attachment ring 24 materials include stainless steel, nickel-cobalt alloys such as MP35N, tantalum and its alloys, polymeric materials, composites, and the like. Attachment ring 24 (as well as all stents and attachment rings described herein) may be configured to self-expand from the illustrated radially constrained state.

Figure 5:
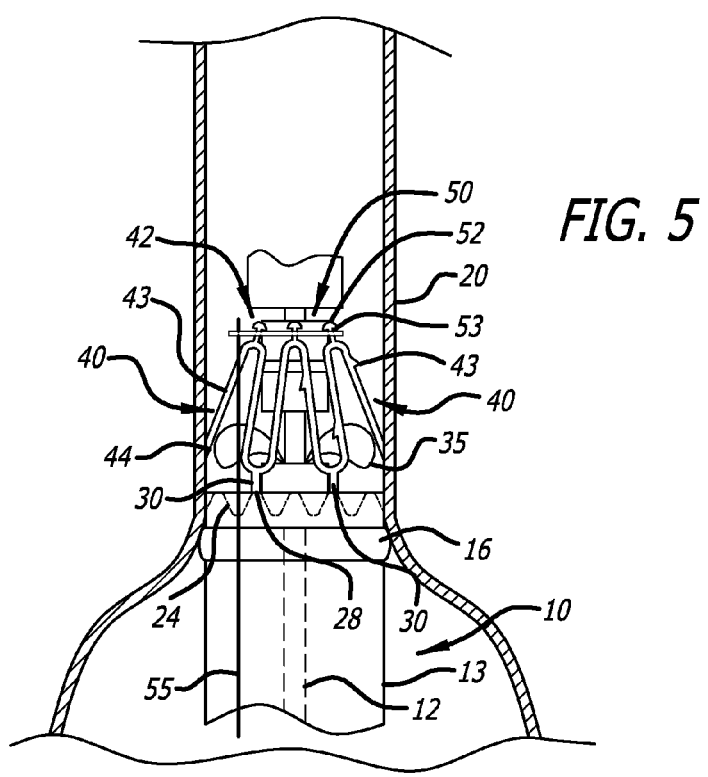
FIG. 5 shows a portion of an endovascular graft according to an embodiment of the present invention partially deployed within the internal vasculature of the patient.
Figure 6:
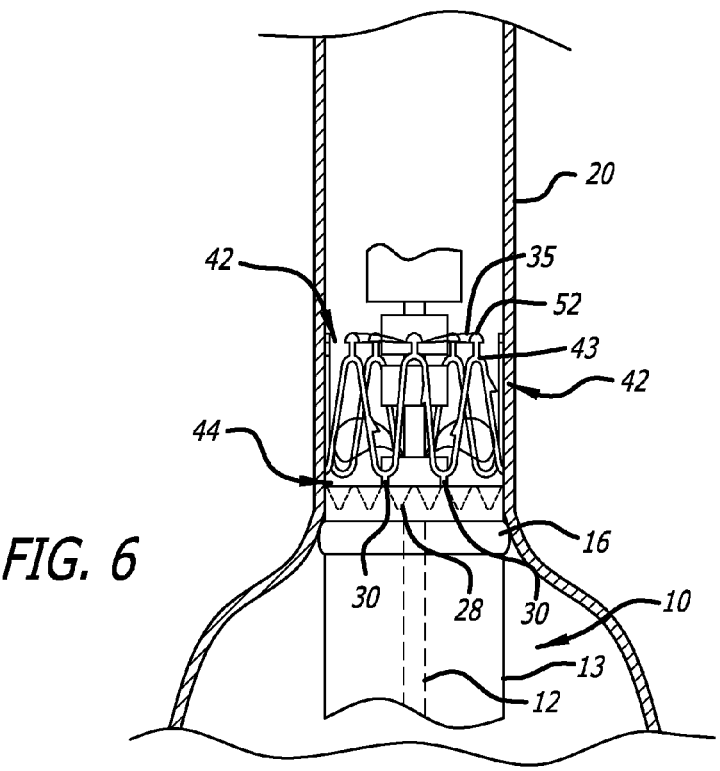
FIG. 6 shows the endovascular graft portion of FIG. 5 fully deployed within the internal vasculature of the patient.

Some apices 28 may also comprise a attachment ring connector element 30 (see FIGS. 5 and 6). The number of connector elements 30 may vary and can be distributed, for example, on every apex, every third or fourth apex, or any other pattern are within the scope of the present invention.

Graft 10 further comprises one or more stents 40 having, in the deployed state (see FIG. 6), a generally free end 42 and a connection end 44. FIGS. 1 and 5-6 illustrate a proximal stent 40, but the stents 40 may additionally or alternatively be provided on the distal end of the graft 10. In the case of a bifurcated graft, a stent 40 may be provided on the distal end of each leg of the bifurcated graft.

As shown in FIGS. 1 and 5-6, stent 40 is typically, though not necessarily, made a part of graft 10 by having the connection end 44 affixed or connected to attachment ring 24 via connector elements as described in detail below. The connection end 44 of stent 40 may also be affixed or embedded directly to or in neck portion 23 and/or other portions of graft body section 13. In addition, the attachment ring and the stent may not be mechanically or otherwise fastened to one another but rather unified, formed of a monolithic piece of material, such as NiTi.

This configuration of stent 40, attachment ring 24, neck portion 23, and cuff 16 helps to separate the sealing function of cuff 16, which requires conformation and apposition to the vessel wall within which graft 10 is deployed without excessive radial force, from the anchoring function of stent 40 (attachment ring 24 and neck portion 23 play intermediate roles). As will be described in more detail hereinafter, the stents 40 of the present invention permit improved positioning of the graft 10 prior to stent anchoring, thereby facilitating better placement and sealing of the graft 10.

Figure 2:
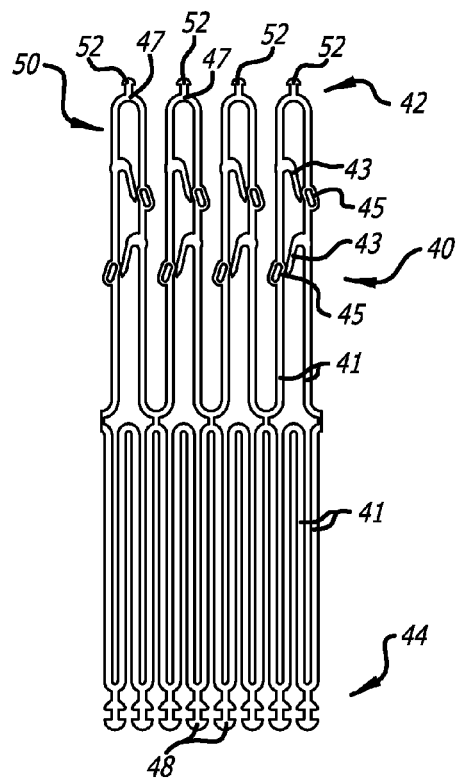
FIG. 2 shows a flat pattern of an embodiment of a stent in accordance with the present invention.
Figure 3:
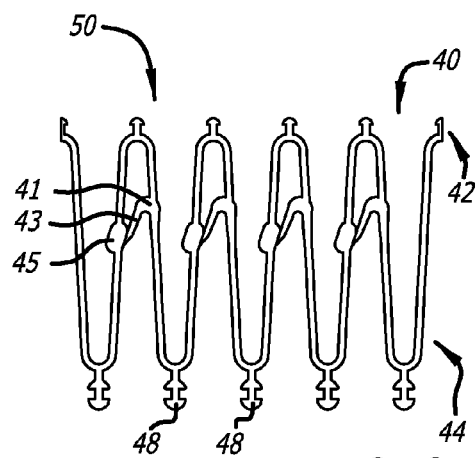
FIG. 3 shows a flat pattern of an alternative embodiment of a stent in accordance with the present invention.
Figure 4:
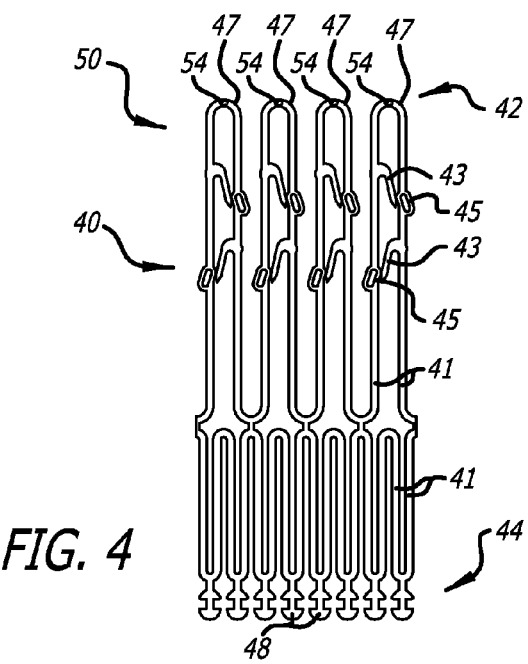
FIG. 4 shows a flat pattern of another alternative embodiment of a stent in accordance with the present invention.

Referring to FIGS. 2-4, each stent 40 of the present invention generally comprises a series of interconnected struts 41. As illustrated, the struts 41 can have various configurations and lengths. Each stent 40 further comprises stent connector elements 48 at the connection end 44 thereof. The stent connector elements 48 are configured to be affixed or otherwise connected to attachment ring connector elements 30 via coupling members (not shown), for example, threads or wires. The stents 40 may be manufactured from any suitable material, including the materials suitable for attachment ring 24. When manufactured from a shape memory alloy having superelastic properties such as NiTi, the stents 40 may be configured to self-expand upon release from the contracted state. The strut structure is often formed as a flat structure, as illustrated in FIGS. 2-4, and thereafter, wrapped and connected in a cylindrical or other configuration, as illustrated in FIG. 1.

Each stent 40 includes one or more barbs 43. A barb 43 can be any outwardly directed protuberance, typically terminating in a sharp point that is capable of at least partially penetrating a body passageway in which graft 10 is deployed (typically the initial and medial layers of a blood vessel such as the abdominal aorta). The number of barbs, the length of each barb, each barb angle, and the barb orientation may vary from barb to barb within a single stent 40 or between multiple stents 40 within a single graft. Although the various barbs 43 (and tuck pads 45 discussed below) may be attached to or fixed on the stent struts 41, it is preferred that they be integrally formed as part of the stent struts 41, as shown in the various figures.

When stent 40 is deployed in the abdominal aorta, for example, typically in a location proximal to the aneurysm and any diseased tissue, barbs 43 are designed to work in conjunction with the distally-oriented blood flow field in this location to penetrate tissue and prevent axial migration of graft 10. As such, the barbs 43 in the FIG. 1 embodiment are oriented distally with respect to graft body section 13. However, the number, dimensions, configuration and orientation of barbs 43 may vary significantly, yet be within the scope of the present invention.

Struts 41 may also comprise optional integral tuck pads 45 disposed opposite each barb 43. During preparation of graft 10 (and therefore the stents 40) into its reduced diameter delivery configuration, each barb 43 is placed behind a corresponding strut 41 and/or optional tuck pad 45, if present, to thereby prevent the barbs 43 from contacting the inside of a delivery sheath or catheter during delivery of the device and from undesired contact with the inside of a vessel wall. As described in U.S. Pat. No. 6,761,733 to Chobotov et al., the complete disclosure of which is incorporated herein by reference, an initial stage release belt 35 disposed about the struts 41 retain the stent 40 in this delivery configuration. The initial stage release belts 35 retain the contracted stent 40 on a guidewire chassis 12 or the like.

The number of initial stage belts 35 varies in accordance with the structure of the stent 40. For example, the stents 40 as illustrated in FIGS. 2 and 4 have proximal and distal segments and two corresponding initial stage belts 35, one about the proximal segment and one about the distal segment, are used to secure the stent 40 as shown in FIG. 1. In shorter stents 40 having a single segment, like the stent 40 illustrated in FIG. 3, a single initial stage belt 35 is typically used to secure the stent 40. Upon deployment of the stent 40, by releasing the initial stage belt(s) 35, the radial expansion of stent 40 results in a displacement of struts 41 so that the distance between them increases. As the struts 41 separate, the barbs 43 are freed from behind the struts 41 and optional tuck pads 45, if present, and engage the wall of the vessel being treated. To enhance the engagement of the barbs 43 in the vessel wall 20, the barbs 43 may be designed to work in conjunction with the distally-oriented blood flow field, that is, the barbs 43 are oriented distally, however, they do not have to be. In the illustrative embodiment, the barbs 43 at the proximal end are oriented distally, while the barbs 43 at the distal end are oriented proximally.

While secure engagement of the barbs 43 in the vessel wall 20 is desirable to prevent axial migration of graft 10, such engagement is generally permanent and not subject to modification. Attempts to reposition the stent 40 or graft 10 after engagement of the barbs 43 in the vessel wall 20 may cause tearing or other damage to the vessel wall 20.

Referring to FIGS. 2-4, each stent 40 of the present invention includes a belt retaining structure 50 provided along the crowns 47 at the free end 42 of the stent 40. In the embodiments illustrated in FIGS. 2 and 3, the belt retaining structure 50 includes a plurality of mushroom shaped connectors 52 extending from the crowns 47. The mushroom shaped connectors 52 may be provided at each crown 47, as illustrated, or in any configuration with respect to the crowns 47. Referring to FIGS. 1 and 5, a releasable secondary stage belt 53 is positionable about the mushroom shaped connectors 52 to retain the stent free end 42 in a contracted state until the secondary stage belt 53 is released, for example, via a release wire 55. In the embodiment illustrated in FIG. 4, the belt retaining structure 50 includes a through hole 54 provided in a plurality of the crowns 47. A releasable belt (not shown) is threaded through the through holes 54 and pulled tight to retain the stent free end 42 in a contracted state until the belt is released. Other belt retaining structures 50 along the stent free end 42 may also be utilized.

As shown in FIG. 5, upon release of the initial stage belts 35, the stent connection end 44, the attachment ring 24, and the graft 10 expand while the secondary stage belt 53 engages the belt retaining structure 50 and retains the stent free end 42 in the generally contracted condition. The stent connection end 44 and the graft 10 expand based on the self expanding nature of the stent 40 and also the force of the distal fluid flow into the graft 10. The struts 41 and barbs 43 are configured such that when the belt retaining structure 50 is in place and the stent free end 42 is restrained, the barbs 43 do not extend sufficiently radially to engage the vessel wall 20, but instead remain spaced therefrom. As such, the graft 10 and stent 40 may be moved and repositioned without the barbs 43 engaging and damaging the vessel wall 20. In at least one embodiment of the invention, the barbs 43 are axially positioned closer to the stent free end 42 than the stent connection end 44 to further ensure the barbs 43 will not contact the vessel wall 20 in the partially deployed state.

Once the stent 40 and graft 10 are positioned as desired, the release wire 55 may be pulled to release the secondary stage belt 53 from the belt retaining structure 50, thereby allowing the stent 40 to fully deploy as illustrated in FIG. 6. Upon full deployment, the struts 41 are free to fully radially expand such that the barbs 43 engage the vessel wall 20 in a normal manner.

In addition to facilitating manual movement and repositioning of the graft 10 and stent 40, the staged deployment of the stent 40 also facilitates self-alignment of the stent 40 and graft 10. As explained above, upon release of the initial stage belts 35, the graft 10 is free to expand and distal fluid flow flows into the graft 10 and creates a "windsock" effect. That is, the distal fluid flow expands the graft 10 and applies a slight distal force upon the graft 10. This distal force helps to align the graft 10 and the stent 40 within the vessel.

Figure 7:
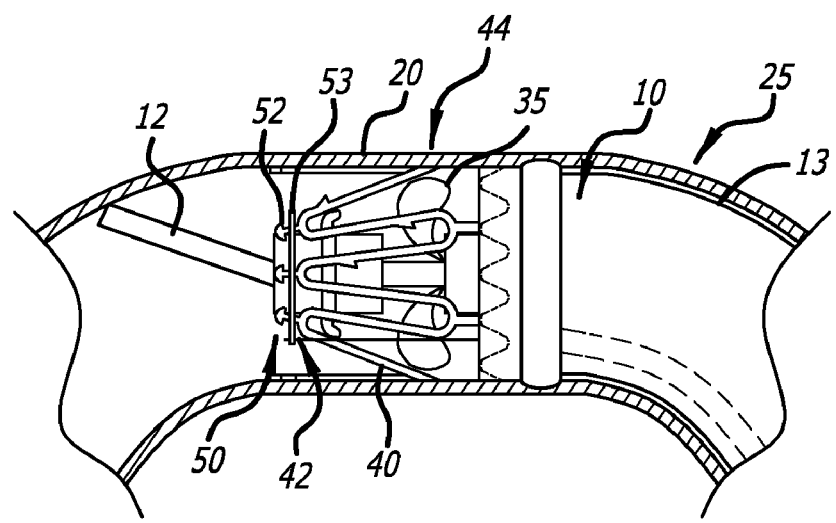
FIG. 7 shows a portion of an endovascular graft according to an embodiment of the present invention partially deployed within an aortic arch of the patient.
Figure 8:
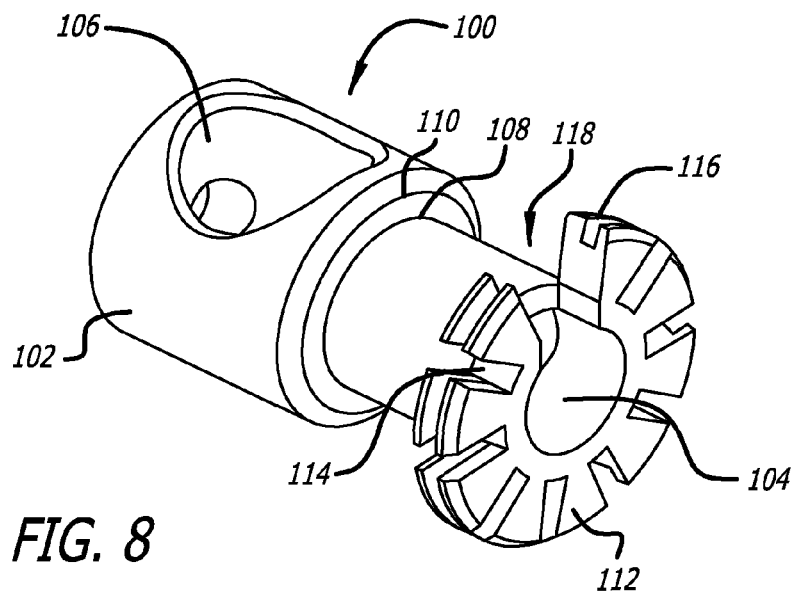
FIG. 8 is an isometric view of a pivot fitting in accordance with another embodiment of the present invention.
Figure 9:
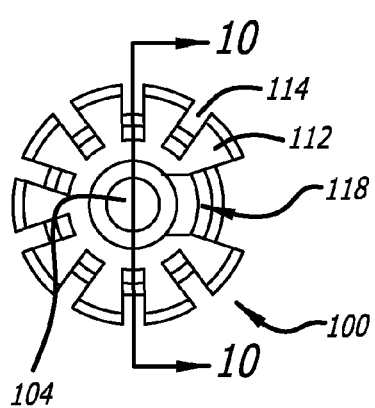
FIG. 9 is an end view of the pivot fitting of FIG. 8.
Figure 10:
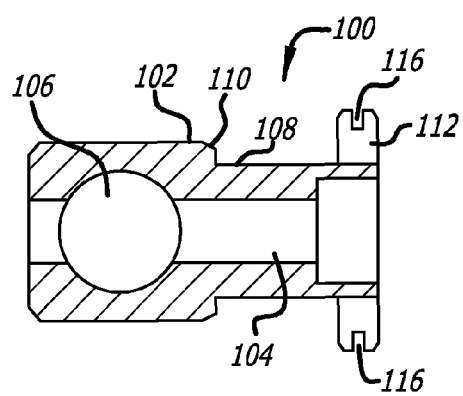
FIG. 10 is a cross-sectional view along the line 10-10 in FIG. 9.

This self alignment is particularly advantageous during deployment of a stent graft within an angulated vessel, for example, in the aortic arch. Referring to FIG. 7, the stent 40 is illustrated partially deployed in an aortic arch 25. The delivery guidewire chassis 12 contacts the vessel wall 20 and does not remain coaxial with respect to the arch 25. As such, in the initial delivery position, the stent 40 may be cocked or otherwise misaligned with respect to the vessel wall 20. In a prior art single stage deployment, the stent would expand and the barbs would engage the vessel wall even if the stent was misaligned. With the stent 40 of the present invention, the initial stage belt(s) 35 are released and the stent 40 is partially deployed. The distal fluid flow flows into the graft 10 and creates the windsock effect, thereby pulling the graft 10 and stent 40 into alignment with the flow and thereby the vessel wall 20.

Referring to FIGS. 8-13, a pivot fitting 100 configured to assist in the multi-staged deployment of stent 40 will be described. The pivot fitting 100 has a generally cylindrical body 102 with an axial through bore 104 configured to position the fitting 100 about the guidewire chassis 12 (see FIG. 13) or the like. A transverse bore 106 is provided to facilitate positioning and attachment of the pivot fitting 100 about the guidewire chassis 12 and loading into the delivery catheter (not shown).

The pivot fitting 100 includes an area 108 of reduced cross section extending between a shoulder 110 and a radial belt support member 112. The area 108 is configured to receive the free ends of the stent 40, for example, the mushroom shaped connectors 52 or the crowns 47 with through holes 54. To facilitate passage of the stent members, the radial belt support member 112 includes a plurality of radial slots 114. In the embodiment illustrated in FIG. 13, each radial slot 114 receives the narrow neck portion of a respective mushroom shaped connector 52.

A circumferential groove 116 is provided along the radial surface of the radial belt support member 112. The circumferential groove 116 is configured to receive and maintain the secondary stage belt 53. A belt radial slot 118 is provided in the radial belt support member 112 to facilitate passage of the secondary stage belt 53 from the guidewire chassis 12 or the like outward to the circumferential groove 116.

Figure 11:
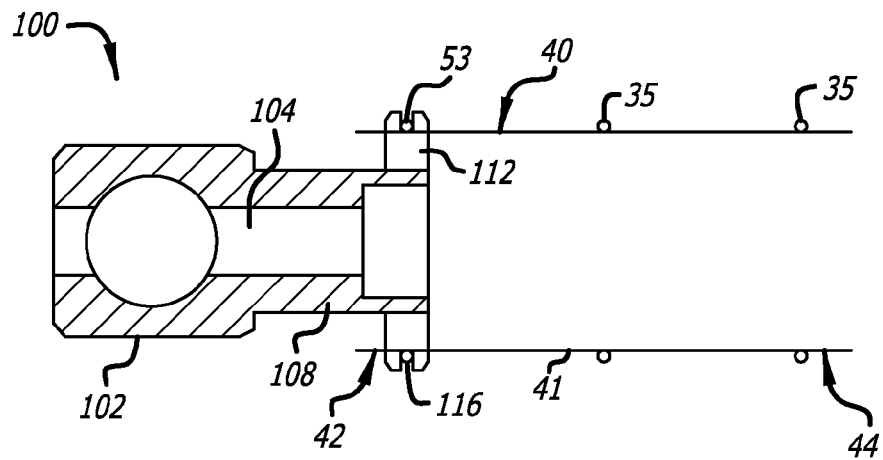
FIG. 11 is a cross-sectional view similar to FIG. 10 illustrating schematically a stent thereon in a contracted state.
Figure 12:
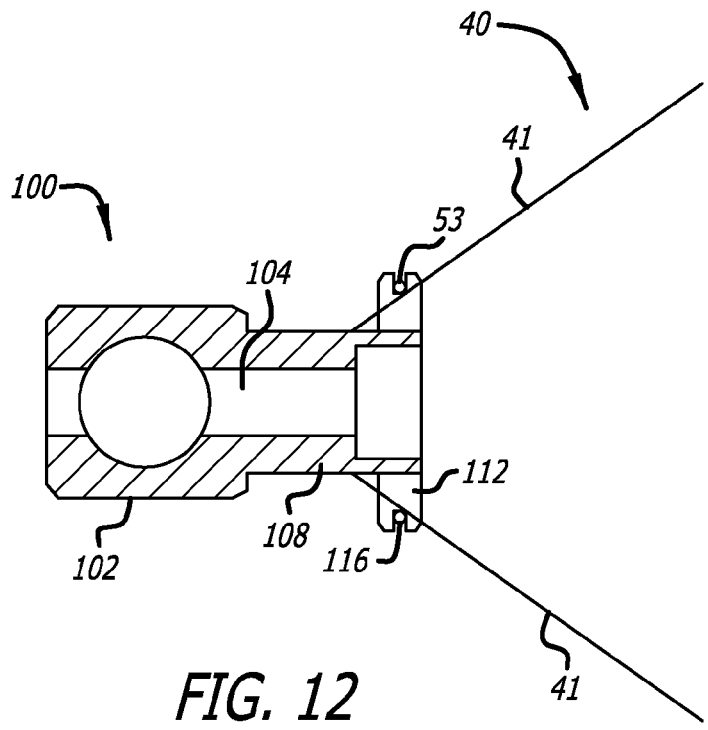
FIG. 12 is a cross-sectional view similar to FIG. 10 illustrating schematically a stent thereon in a partially deployed state.
Figure 13:
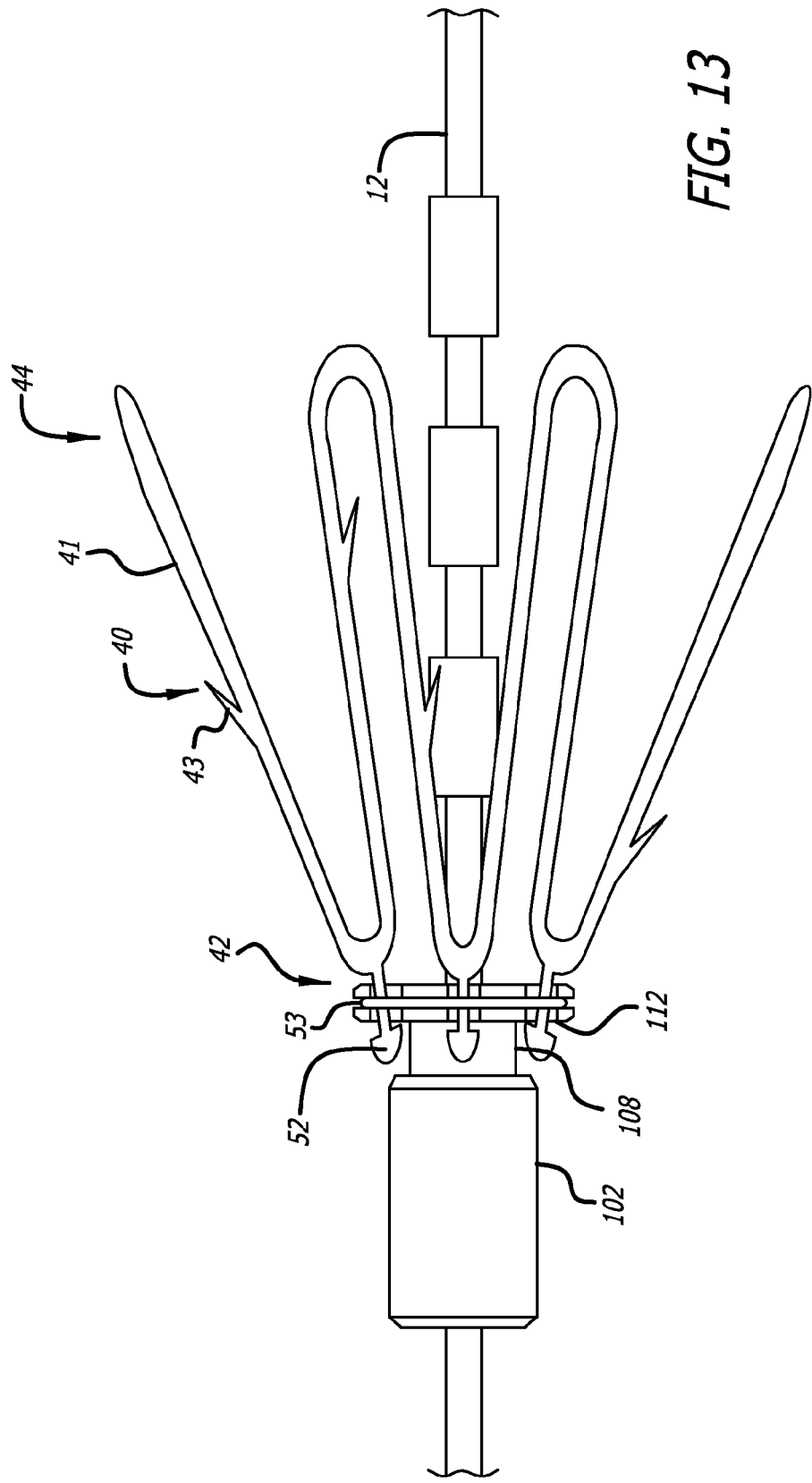
FIG. 13 is a perspective view illustrating a stent in the partially deployed state of FIG. 12.

Referring to FIG. 11, in the delivery stage, the stent 40 is compacted with the free end 42 passing through the radial slots 114 in the radial belt support member 112. The secondary stage belt 53 is secured in the circumferential groove 116 and constrains the stent free end 42. Turning to FIGS. 12 and 13, upon release of the initial stage release belts 35, the connection end 44 of the stent 40 expands while the free end 42 is retained by the secondary stage belt 53. The opening diameter of the connection end 44 can be controlled by the relation of the outer diameter of area 108 and the inner diameter of the circumferential groove 116 and the length of the portion of the stent free end 42 that extends into area 108. In this partially deployed state, the stent free end 42 is securely retained by the pivot fitting 100, which in turn is connected to the guidewire chassis 12. As such, movement of the guidewire chassis 12 provides relatively precise control of the position of the stent 40. Once the stent 40 is positioned in a desired position, the secondary stage belt 53 is released and the stent free end 42 disengages from the pivot fitting 100 and expands. The pivot fitting 100 remains connected to the guidewire chassis 12 and is removed upon removal thereof.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A stent-graft system comprising:
   a graft member;
   a stent having a connection end interconnected with the graft member and a free end opposed thereto;
   a belt retaining structure provided at the stent free end;
   a belt releasably engaging the belt retaining structure and configured to constrain the stent free end substantially independent of the stent connection end; and
   a pivot fitting configured to retain the belt about the belt retaining structure such that the belt pivotally secures the stent free end to the pivot fitting.

2. The stent-graft system according to claim 1 wherein the pivot fitting is attached to a graft delivery member.

3. The stent-graft system according to claim 2 wherein the pivot fitting includes an axial bore configured to receive the graft delivery member.

4. The stent-graft system according to claim 1 wherein the pivot fitting includes a radial belt support member with a circumferential groove configured to receive the belt.

5. The stent-graft system according to claim 4 wherein the radial belt support member includes a plurality of radial slots configured to receive respective portions of the stent free end.

6. The stent-graft system according to claim 4 wherein the pivot fitting includes an area of reduced cross section configured to receive the belt retaining structure and a diameter of the stent connection end in the partially deployed state is determined at least in part by the relationship of an outer diameter of the area of reduced cross section and an inner diameter of the circumferential groove.

* * * * *